United States Patent
Park et al.

(10) Patent No.: US 9,790,236 B2
(45) Date of Patent: Oct. 17, 2017

(54) ORGANIC SEMICONDUCTOR COMPOUND, AND TRANSISTOR AND ELECTRONIC DEVICE INCLUDING THE SAME

(75) Inventors: Jeong-il Park, Seongnam-si (KR); Bang Lin Lee, Suwon-si (KR); Jong Won Chung, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 312 days.

(21) Appl. No.: 13/349,141

(22) Filed: Jan. 12, 2012

(65) Prior Publication Data
US 2012/0168729 A1     Jul. 5, 2012

Related U.S. Application Data

(63) Continuation-in-part of application No. 13/187,996, filed on Jul. 21, 2011.

(30) Foreign Application Priority Data

Jan. 5, 2011 (KR) ................ 10-2011-0000850

(51) Int. Cl.
| | | |
|---|---|---|
| C07D 513/06 | (2006.01) | |
| C07D 495/06 | (2006.01) | |
| H01L 51/00 | (2006.01) | |
| H01L 51/05 | (2006.01) | |

(52) U.S. Cl.
CPC ......... *C07D 513/06* (2013.01); *C07D 495/06* (2013.01); *H01L 51/0036* (2013.01); *H01L 51/0043* (2013.01); *H01L 51/0068* (2013.01); *H01L 51/0071* (2013.01); *H01L 51/0558* (2013.01)

(58) Field of Classification Search
CPC ... C07D 239/26; C07D 495/06; C07D 513/06
USPC .............. 514/250; 544/338; 257/40
See application file for complete search history.

(56) References Cited

U.S. PATENT DOCUMENTS

| | | |
|---|---|---|
| 7,745,819 B2 | 6/2010 | Lee et al. |
| 8,348,635 B2 | 1/2013 | Yamashita et al. |

FOREIGN PATENT DOCUMENTS

| | | |
|---|---|---|
| CN | 101080478 | 11/2007 |
| JP | 2006-216814 A | 8/2006 |
| JP | 2007-317984 A | 12/2007 |
| JP | 2008-521243 A | 6/2008 |
| JP | 2008-109135 | 8/2008 |
| JP | 2009027117 A | 2/2009 |
| JP | 2009-191754 A | 8/2009 |
| JP | 2010-275239 A | 12/2010 |
| WO | WO-2007004799 A1 | 1/2007 |

OTHER PUBLICATIONS

King, Med. Chem., Principle and Practice (1994), pp. 206-208.*
King Ref. was submitted to applicant in U.S. Appl. No. 13/187,996.*
Chinese Office Action dated Oct. 27, 2014 issued in corresponding Chinese Application No. 201210001830.7.
Lin, et al. "Thiazole-Based Organic Semiconductors for Organic Electronics", Advanced Materials, vol. 24, pp. 3087-3106 (2012).
Japanese Office Action dated Sep. 1, 2015, issued in corresponding Japanese Application No. 2012-000700 (English translation provided).
Notice of Allowance dated Jan. 5, 2016 issued in corresponding Japanese Application No. 2012-000700 (Partial English translation provided).
Tsai, et al., "An unprecedentedly huge square-grid copper(II)-organic framework material built from a bulky pyrene-derived elongated cross-shaped scaffold" Inorganic Chemistry (2009), 48(18), 8650-8652.
Wehr, "Polymere Bis(oxazolo)pyrene", Die Makromolekulare Chemie (1976), 177(2), 351-7.

* cited by examiner

*Primary Examiner* — Taofiq A Solola
(74) *Attorney, Agent, or Firm* — Harness, Dickey & Pierce, P.L.C.

(57) ABSTRACT

An example embodiment relates to an organic semiconductor compound, represented by Chemical Formula 1 herein, which may be polymerized and used in transistors and electronic devices. The organic semiconductor compound includes a base structure of four fused benzene rings with functional groups $R^1$ to $R^3$ connected to a first benzene ring and with functional groups $R^4$ to $R^6$ connected to a second benzene ring. The base structure's third and fourth benzene rings are connected to $X^1$, $X^2$ and $X^3$, $X^4$ respectfully. At least one of $X^1$ and $X^2$ is a sulfur atom. At least one of $X^3$ and $X^4$ is a sulfur atom. The base structure further includes functional groups $R^7$ and $R^8$.

20 Claims, 3 Drawing Sheets

ORGANIC SEMICONDUCTOR COMPOUND, AND TRANSISTOR AND ELECTRONIC DEVICE INCLUDING THE SAME

CROSS-REFERENCE TO RELATED APPLICATION

This application is a continuation-in-part of U.S. application Ser. No. 13/187,996 filed on Jul. 21, 2011, and claims priority under 35 U.S.C. §119 to Korean Patent Application No. 10-2011-0000850 filed on Jan. 5, 2011, the entire contents of each of which are hereby incorporated herein by reference.

BACKGROUND

1. Field

Some example embodiments relate to an organic semiconductor compound and a transistor and an electronic device including the same.

2. Description of the Related Art

Progressing to the information-oriented society requires developing a new image display device of which the drawbacks of the conventional cathode ray tube (CRT) with a heavy weight and a large volume are improved. Accordingly, several flat panel displays such as a liquid crystal display (LCD), an organic light emitting diode (OLED) display, a plasma display panel (PDP), a surface-conduction electron-emitter display (SED), and so on are drawing attention.

A thin film transistor (TFT) including a semiconductor layer of amorphous silicon is widely used for a switching device of the flat panel displays.

The amorphous silicon thin film transistor is widely used since it has good uniformity and high electrical characteristics in a doping state, while it has good insulating characteristics in a non-doping state.

However, in order to deposit the conventional amorphous silicon thin film transistor on a substrate, there are limits in carrying out the process at a high temperature of 300° C. Therefore, it is difficult to apply it to a polymer substrate for accomplishing a flexible display.

An organic thin film transistor (OTFT) generally includes a substrate, a gate electrode, an insulation layer, a source electrode, a drain electrode, and a channel region. It may be classified as a bottom contact (BC) type in which a channel region is formed on the source electrode and the drain electrode, and a top contact (TC) type in which a metal electrode is formed on the channel region due to mask deposition.

The low molecular or oligomer organic semiconductor material filled in the channel region of the organic thin film transistor (OTFT) includes merocyanine, phthalocyanine, perylene, pentacene, C60, a thiophene oligomer, and so on. The low molecular or oligomer organic semiconductor material may be a thin film formed on the channel region mainly according to a vacuum process.

Organic semiconductor polymer materials have workability in that large-area processing is capable using a solution method such as printing techniques at a low cost.

SUMMARY

An example embodiment provides an organic semiconductor compound having excellent charge mobility, and being fabricated using a solution process and an organic semiconductor polymer obtained from a polymerization thereof.

Another example embodiment provides a transistor including the organic semiconductor compound or organic semiconductor polymer.

Another example embodiment provides an electronic device including the organic semiconductor compound or organic semiconductor polymer.

According to an example embodiment, an organic semiconductor compound represented by the following Chemical Formula 1 is provided.

[Chemical Formula 1]

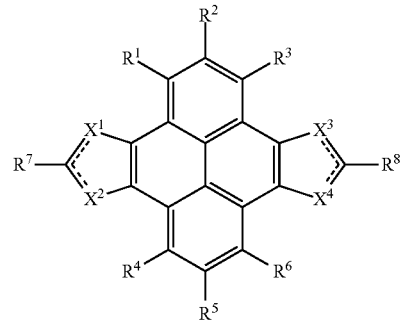

In Chemical Formula 1,
at least one of $X^1$ and $X^2$ is S, and at least one of $X^3$ and $X^4$ is S, $X^1$ to $X^4$ are each independently one of S, N and $CR^{50}$, wherein $R^{50}$ is one of hydrogen, a substituted C1 to C20 linear alkyl group, a substituted C1 to C20 branched alkyl group, an unsubstituted C1 to C20 linear alkyl group, an unsubstituted C1 to C20 branched alkyl group, and a substituted or unsubstituted C6 to C20 aryl group.

$R^1$ to $R^6$ are each independently one of (i) hydrogen, a halogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C1 to C20 alkoxy group, a substituted or unsubstituted C3 to C20 cycloalkyloxy group, a substituted or unsubstituted C6 to C30 aryl group, a substituted or unsubstituted C6 to C30 aryloxy group, a substituted or unsubstituted C2 to C30 heteroaryl group, a C2 to C30 heteroaromatic ring group including at least one electron withdrawing imine nitrogen atom, a C2 to C30 heteroaromatic ring group including at least one sulfur atom, $NR^{51}R^{52}$, $C(O)OR^{53}$, $C(O)NR^{54}R^{55}$ a combination thereof, and (ii) structured so two adjacent substituents of $R^1$ to $R^6$ are linked to each other to provide one of a thiophenyl ring group fused with a pyrene moiety and a thiazolyl ring group fused with a pyrene moiety, wherein $R^{51}$ to $R^{55}$ are each independently one of hydrogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C6 to C30 aryl group, a substituted or unsubstituted C2 to C30 heteroaryl group, and a combination thereof, and $R^7$ and $R^8$ are each independently one of hydrogen, halogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C1 to C20 alkoxy group, a substituted or unsubstituted C3 to C20 cycloalkyloxy group, a substituted or unsubstituted C6 to C30 aryl group, a substituted or unsubstituted C6 to C30 aryloxy group, a substituted or unsubstituted C2 to C30 heteroaryl group, a C2 to C30 heteroaromatic ring group including at least one electron withdrawing imine nitrogen atom, a C2 to C30 heteroaromatic ring group including at least one sulfur atom, $NR^{51}R^{52}$, $C(O)OR^{53}$, $C(O)NR^{54}R^{55}$ and a combination thereof, provided that (i) when at least one of $X^1$ and $X^2$ is S, and the other one of $X^1$ and $X^2$ is $CR^{50}$, and (ii) when at least one of $X^3$ and $X^4$ is S, and the other one is $CR^{50}$, at least one of $R^1$ to $R^6$ is one of (i) a C2 to C30 heteroaromatic ring group including at least one electron withdrawing imine nitrogen atom, and (ii) two adjacent substituents of $R^1$ to $R^6$ are linked to each other to provide one of a thiophenyl ring group fused with a pyrene moiety and a thiazolyl ring group fused with a pyrene moiety.

The organic semiconductor compound of Chemical Formula 1 may be an organic semiconductor compound represented by the following Chemical Formula 2.

[Chemical Formula 2]

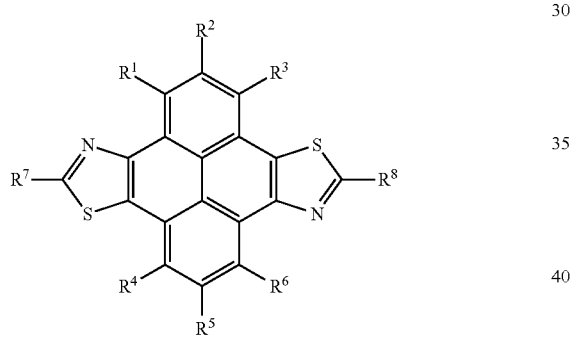

In Chemical Formula 2, $R^1$ to $R^8$ are the same as in Chemical Formula 1.

The C2 to C30 heteroaromatic ring group including at least one electron withdrawing imine nitrogen atom may include functional groups represented by the following Chemical Formula 3.

[Chemical Formula 3]

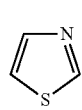 (3-1)

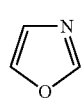 (3-2)

 (3-3)

 (3-4)

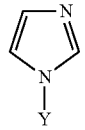 (3-5)

 (3-6)

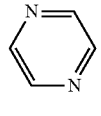 (3-7)

 (3-8)

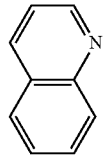 (3-9)

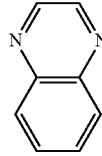 (3-10)

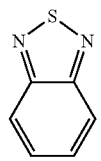 (3-11)

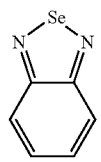 (3-12)

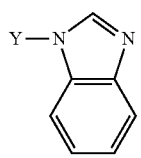 (3-13)

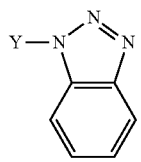 (3-14)

-continued

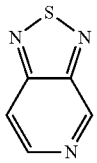
(3-15)

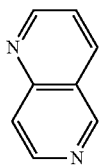
(3-16)

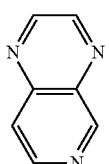
(3-17)

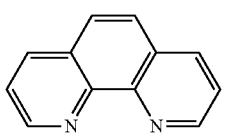
(3-18)

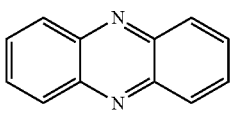
(3-19)

In Chemical Formula 3,

Y is one of hydrogen, a C1 to C20 linear or branched alkyl group, a C3 to C20 cycloalkyl group, a C6 to C30 aryl group, a C1 to C16 linear or branched alkoxy group, or a C3 to C16 cycloalkoxyalkyl group.

The C2 to C30 heteroaromatic ring group including at least one electron withdrawing imine nitrogen atom may include one of a thiazolyl group, a thiadiazolyl group, an isoxazolyl group, an oxadiazolyl group, an imidazolyl group, a pyrazolyl group, a trizolyl group, tetrazolyl group, a pyridyl group, a pyridazinyl group, a quinolinyl group, an isoquinolinyl group, a quinoxalinyl group, a naphthyridinyl group, a benzoimidazolyl group, a pyrimidopyrimidinyl group, a benzothiadiazolyl group, a benzoselenadiazolyl group, a benzotriazolyl group, a benzothiazolyl group, a benzoxazolyl group, a phenanthrolinyl group, a phenazinyl group, a phenanthridinyl group, and a combination thereof.

The C2 to C30 heteroaromatic ring group including at least one sulfur atom may be one of the groups represented by the following Chemical Formula 4.

[Chemical Formula 4]

(4-1)

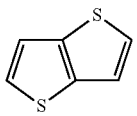
(4-2)

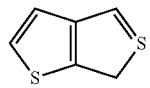
(4-3)

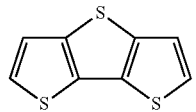
(4-4)

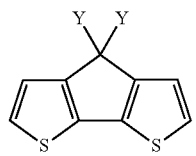
(4-5)

In Chemical Formula 4,

Y is one of hydrogen, a C1 to C20 linear or branched alkyl group, a C3 to C20 cycloalkyl group, a C6 to C30 aryl group, a C1 to C16 linear or branched alkoxy group, and a C3 to C16 cycloalkoxyalkyl group. Y may be present in plural, and a plurality of Y may be the same or different.

In Chemical Formula 1, $R^7$ and $R^8$ may be one of a thiophenyl group, a thiazolyl group, a thiadiazolyl group, an isoxazolyl group, an oxadiazolyl group, an imidazolyl group, a pyrazolyl group, a trizolyl group, a tetrazolyl group, a pyridyl group, a pyridazinyl group, a quinolinyl group, an isoquinolinyl group, a quinoxalinyl group, a naphthyridinyl group, a benzoimidazolyl group, a pyrimidopyrimidinyl group, a benzothiadiazolyl group, a benzoselenadiazolyl group, a benzotriazolyl group, a benzothiazolyl group, a benzoxazolyl group, a phenanthrolinyl group, a phenazinyl group, a phenanthridinyl group, and a combination thereof.

According to another example embodiment, an organic semiconductor polymer including a structural unit represented by the following Chemical Formula 5 is provided.

[Chemical Formula 5]

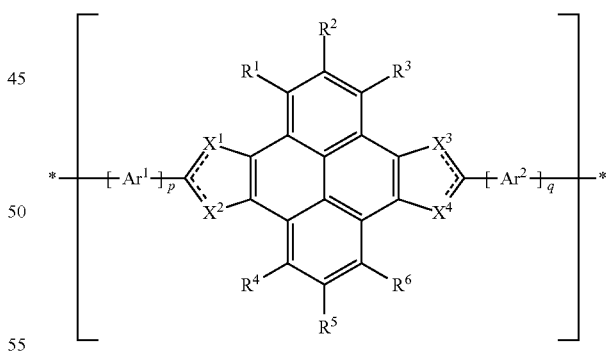

In Chemical Formula 5, $X^1$ to $X^4$ and $R^1$ to $R^6$ may be the same as in Chemical Formula 1, and $Ar^1$ and $Ar^2$ are each independently one of a substituted or unsubstituted C6 to C30 aromatic ring group, a substituted or unsubstituted C4 to C14 heteroaromatic ring group, and a substituted or unsubstituted C6 to C30 condensed polycyclic group, p and q are each independently integers ranging from 0 to 10, and when p or q are each 2 or more, a plurality of $Ar^1$ and $Ar^2$ are the same or different from each other.

The organic semiconductor polymer including the structural unit represented by Chemical Formula 5 may be an organic semiconductor polymer including a structural unit represented by the following Chemical Formula 6.

[Chemical Formula 6]

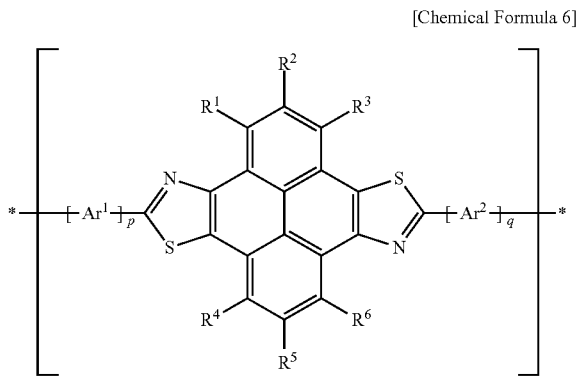

In Chemical Formula 6,
$R^1$ to $R^6$ may be the same as in Chemical Formula 1, and $Ar^1$ and $Ar^2$ may be the same as in Chemical Formula 5. The $Ar^1$ and $Ar^2$ may include at least one thiophenyl group, and may be represented by the following Chemical Formula 7.

[Chemical Formula 7]

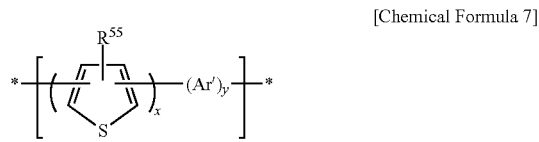

In Chemical Formula 7, $R^{55}$ is one of hydrogen and a C1 to C20 alkyl group, Ar' is one of a C6 to C30 arylene group, a C6 to C30 condensed polycyclic group, a C2 to C30 heteroaromatic ring group, a C2 to C30 heteroaromatic ring group including at least one electron withdrawing imine nitrogen atom, a C2 to C30 heteroaromatic ring group including at least one sulfur atom, and a combination thereof, and x is an integer ranging from 1 to 7, and y is an integer ranging from 0 to 4.

In Chemical Formula 7, the thiophenyl structural unit and Ar' structural unit may be alternately arranged, or randomly arranged each other. The C2 to C30 heteroaromatic ring group including at least one electron withdrawing imine nitrogen atom, a C2 to C30 heteroaromatic ring group including at least one sulfur atom are the same as described above.

The $Ar^1$ and $Ar^2$ may be one of a substituted or unsubstituted phenylene group, a substituted or unsubstituted thiophene group, a substituted or unsubstituted benzothiophene group, a substituted or unsubstituted thienothiophene group, a substituted or unsubstituted thiazole group, a substituted or unsubstituted thiazolothiazole group, a substituted or unsubstituted fluorene group, a substituted or unsubstituted carbazole group, and a combination thereof.

The organic semiconductor polymer including the structural unit represented by Chemical Formula 5 may include one of the compounds represented by the following Chemical Formulae 8-1 to 8-4.

[Chemical Formula 8-1]

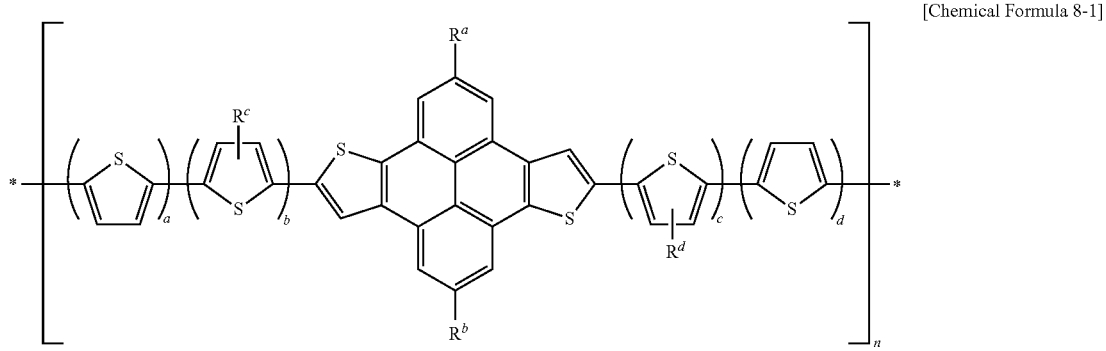

[Chemical Formula 8-2]

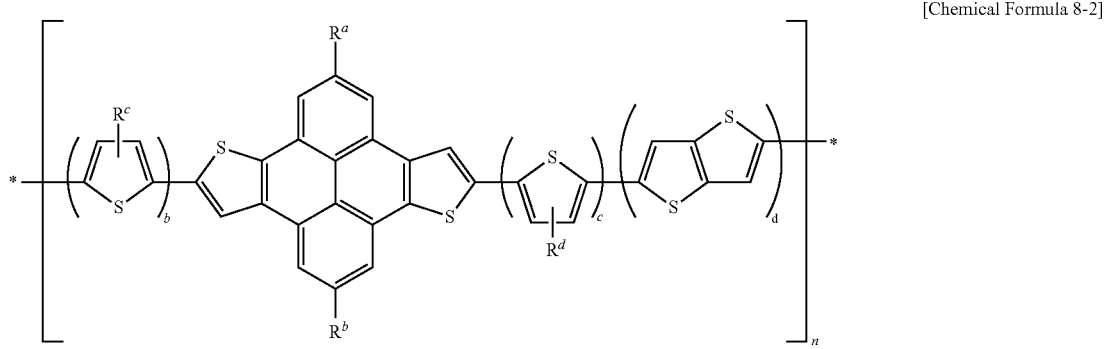

In Chemical Formulae 8-1 and 8-2, $R^a$ and $R^b$ are one of (i) a C1 to C10 alkyl group or a C2 to C30 heteroaromatic ring group including at least one electron withdrawing imine nitrogen atom, and (ii) $R^a$ or $R^b$ may form one of a thiophenyl ring group fused with a pyrene moiety and a thiazolyl ring group fused with a pyrene moiety, provided that at least one of $R^a$ and $R^b$ is a C2 to C30 heteroaromatic ring group including at least one electron withdrawing imine nitrogen atom, and one of $R^a$ and $R^b$ forms one of a thiophenyl ring group fused with a pyrene moiety and a thiazolyl ring group fused with a pyrene moiety, $R^c$ and $R^d$ is a C1 to C20 alkyl group such as a dodecyl group, a, b, c, and d are integers ranging from 0 to 10, and a+b and c+d are 10 or less, and n is a polymerization degree of a polymer.

The transistor includes (i) a gate electrode positioned on a substrate, (ii) a source electrode and a drain electrode on the substrate, the source electrode and the drain electrode facing each other and defining a channel region, (iii) an insulation layer on the substrate, the insulation layer electrically insulating the source electrode, the drain electrode, and the gate electrode, and (iv) an active layer in between the source electrode and the drain electrode, the active layer including the organic semiconductor compound.

According to another example embodiment, an electronic device including the organic semiconductor compound or organic semiconductor polymer is provided.

The electronic device may be a solar cell.

Hereinafter, some example embodiments will be described in detail.

[Chemical Formula 8-3]

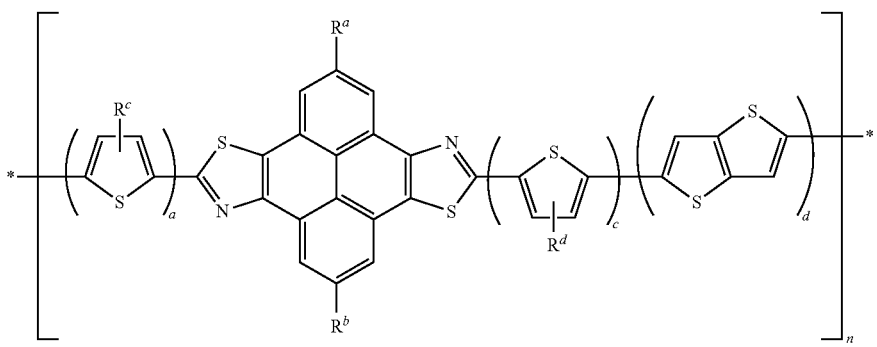

[Chemical Formula 8-4]

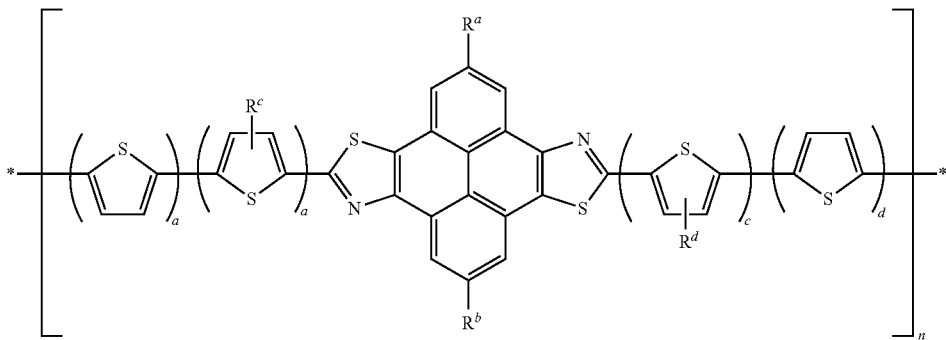

In Chemical Formulae 8-3 and 8-4, $R^a$ and $R^b$ are one of (i) a C1 to C10 alkyl group such as a t-butyl group or a C2 to C30 heteroaromatic ring group including at least one electron withdrawing imine nitrogen atom, and (ii) $R^a$ or $R^b$ may form a thiophenyl ring group or a thiazolyl ring group fused with a pyrene moiety, $R^c$ and $R^d$ are a C1 to C20 alkyl group such as a dodecyl group, a, b, c, and d are integers ranging from 0 to 10, and a+b and c+d are 10 or less, and n is a polymerization degree of a polymer.

The organic semiconductor polymer may have a number average molecular weight (Mn) of about 5000 to about 200,000, and specifically about 10,000 to about 100,000.

The organic semiconductor compound or polymer may be a p-type organic semiconductor compound or organic semiconductor polymer.

According to another example embodiment, a transistor including the organic semiconductor compound or organic semiconductor polymer is provided.

BRIEF DESCRIPTION OF THE DRAWINGS

Some example embodiments will be more clearly understood from the following brief description taken in conjunction with the accompanying drawings, in which.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of like reference numbers in the various drawings is intended to indicate the presence of like elements or features throughout the different views.

DETAILED DESCRIPTION

Figure 1:
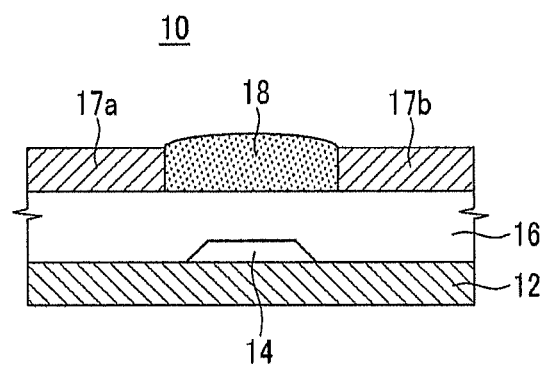
FIG. 1 is a schematic cross-sectional view of a transistor according to an example embodiment.

This disclosure will be described more fully hereinafter with reference to the accompanying drawings, in which some example embodiments of this disclosure are shown. This disclosure may, however, be embodied in many different forms and should not be construed as limited to some of the example embodiments set forth herein.

In the drawings, the thickness of layers, films, panels, etc., are exaggerated for clarity. Like reference numerals designate like elements throughout the specification. It will be understood that when an element such as a layer, film, or substrate is referred to as being "on" another element, it may be directly on the other element or intervening elements may also be present. In contrast, when an element is referred to as being "directly on" another element, there are no intervening elements present.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term "heteroaromatic ring group" may refer to a C2 to C30 heteroaryl group, a C3 to C30 heterocycloalkenyl group, or a C3 to C30 heterocycloalkynyl group. The term "condensed polycyclic group" may refer to a fused ring of the heteroaromatic ring group and at least one cyclic group selected from a C3 to C30 cycloalkyl group, a C3 to C30 cycloalkenyl group, a C2 to C30 heterocycloalkyl group, a C2 to C30 heteroaryl group, and a C3 to C30 heterocycloalkenyl group.

As used herein, when specific definition is not otherwise provided, the prefix "hetero" refers to one including heteroatoms selected from the group consisting of N, O, S, Si, and P, and including 1 to 4 heteroatoms in one ring.

As used herein, when specific definition is not otherwise provided, the term "substituted" refers to one substituted with at least a functional group selected from the group consisting of a fluoro, a C1 to C30 linear or branched alkyl, a C3 to C30 cycloalkyl, a C1 to C20 fluoroalkyl, a C1 to C20 perfluoroalkyl ($C_nF_{2n+1}$), a C1 to C30 linear or branched alkoxy, a C3 to C30 cycloalkoxy, a C2 to C30 linear or branched alkoxyalkyl, a C4 to C30 cycloalkoxyalkyl, and combinations thereof in a functional group or a compound.

According to an example embodiment, an organic semiconductor compound represented by the following Chemical Formula 1 is provided.

[Chemical Formula 1]

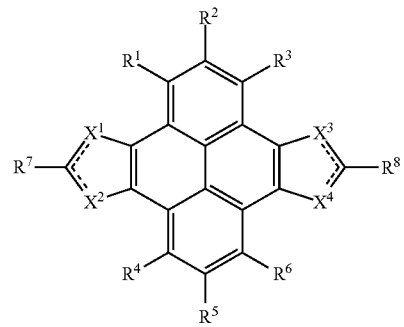

The organic semiconductor compound represented by Chemical Formula 1 includes a base structure of four fused benzene rings with functional groups $R^1$ to $R^3$ connected to a first benzene ring and with functional groups $R^4$ to $R^6$ connected to a second benzene ring. The base structure's third and fourth benzene rings are connected to $X^1$, $X^2$ and $X^3$, $X^4$ respectfully. The base structure further includes functional groups $R^7$ and $R^8$.

In Chemical Formula 1, $X^1$ to $X^4$ are each independently S, N or $CR^{50}$ (wherein $R^{50}$ is selected from hydrogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C6 to C20 aryl group), provided that at least one of $X^1$ and $X^2$ is S, and at least one of $X^3$ and $X^4$ is S, $R^1$ to $R^6$ are each independently selected from hydrogen, halogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C1 to C20 alkoxy group, a substituted or unsubstituted C3 to C20 cycloalkyloxy group, a substituted or unsubstituted C6 to C30 aryl group, a substituted or unsubstituted C6 to C30 aryloxy group, a substituted or unsubstituted C2 to C30 heteroaryl group, a C2 to C30 heteroaromatic ring group including at least one electron withdrawing imine nitrogen atom, a C2 to C30 heteroaromatic ring group including at least one sulfur atom, $NR^{51}R^{52}$, $C(O)OR^{53}$, $C(O)NR^{54}R^{55}$ (wherein $R^{51}$ to $R^{55}$ are each independently hydrogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C6 to C30 aryl group, a substituted or unsubstituted C2 to C30 heteroaryl group, and a combination thereof), and a combination thereof, or two adjacent substituents of $R^1$ to $R^6$ are linked to each other to provide a thiophenyl ring group fused with a pyrene moiety or a thiazolyl ring group fused with a pyrene moiety, and $R^7$ and $R^8$ are each independently selected from hydrogen, a halogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C1 to C20 alkoxy group, a substituted or unsubstituted C3 to C20 cycloalkyloxy group, a substituted or unsubstituted C6 to C30 aryl group, a substituted or unsubstituted C6 to C30 aryloxy group, a substituted or unsubstituted C2 to C30 heteroaryl group, a C2 to C30 heteroaromatic ring group including at least one electron withdrawing imine nitrogen atom, a C2 to C30 heteroaromatic ring group including at least one sulfur atom, $NR^{51}R^{52}$, $C(O)OR^{53}$, $C(O)NR^{54}R^{55}$ (wherein $R^{51}$ to $R^{55}$ are the same as above), and a combination thereof, provided that when at least one of $X^1$ and $X^2$ is S, and the other one of $X^1$ and $X^2$ is $CR^{50}$ (wherein $R^{50}$ is the same as above), and when at least one of $X^3$ and $X^4$ is S, and the other one is $CR^{50}$ (wherein $R^{50}$ is the same as above), at least one of $R^1$ to $R^6$ is a C2 to C30 heteroaromatic ring group including at least one electron withdrawing imine nitrogen atom or two adjacent substituents of $R^1$ to $R^6$ are linked to each other to provide a thiophenyl ring group fused with a pyrene moiety or a thiazolyl ring group fused with a pyrene moiety.

The organic semiconductor compound of Chemical Formula 1 has an excellent coplanarity due to the pyrene mother-structure and has organic semiconductor characteristics due to the thiophenyl ring group or thiazolyl ring group structure fused with the pyrene mother-structure. The organic semiconductor compound having an excellent coplanarity easily transfers charge between molecules to provide good semiconductor characteristics, so it may be effectively used in a transistor. The organic semiconductor compound may be applied to a solar cell or the like since it has good miscibility with CNT, fullerene, graphene or the like.

In the organic semiconductor compound of the above Chemical Formula 1, when the hetero ring group including $X^1$ and $X^2$ and the hetero ring group including $X^3$ and $X^4$ are a thiophenyl group, at least one of $R^1$ to $R^6$ is C2 to C30 heteroaromatic ring group including at least one electron withdrawing imine nitrogen atom, or it may form a thiophenyl ring group or a thiazolyl ring group that the adjacent two substituents of $R^1$ to $R^6$ are connected and fused with a pyrene moiety. Thereby it may decrease the HOMO level, improve the oxidation stability and the electrical reliability of the organic semiconductor compound or the organic semiconductor polymer obtained from the same, and increase the coplanarity, so as to increase the interaction between molecules. Therefore, it may be anticipated to improve the carrier mobility.

In the organic semiconductor compound of the above Chemical Formula 1, when the hetero ring group including $X^1$ and $X^2$ and the hetero ring group including $X^3$ and $X^4$ are a thiazolyl ring group, the electron withdrawing group is included in the hetero ring group to decrease the HOMO level, so that it may improve the oxidation stability and the electrical reliability of the organic semiconductor compound or the organic semiconductor polymer obtained from the same.

In the organic semiconductor compound of the above Chemical Formula 1, $R^7$ and $R^8$ may be a substituted or unsubstituted thiophenyl group.

The organic semiconductor compound of the above Chemical Formula 1 may be an organic semiconductor compound represented by the following Chemical Formula 2.

[Chemical Formula 2]

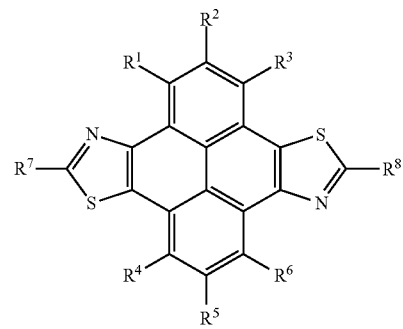

In Chemical Formula 2, $R^1$ to $R^8$ may be the same as in Chemical Formula 1.

The C2 to C30 heteroaromatic ring group including at least one electron withdrawing imine nitrogen atom may include a functional group represented by the following Chemical Formula 3, but is not limited thereto.

[Chemical Formula 3]

  (3-1)

  (3-2)

  (3-3)

  (3-4)

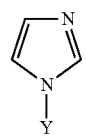  (3-5)

  (3-6)

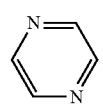  (3-7)

  (3-8)

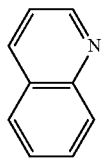 (3-9)

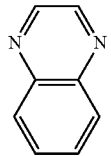 (3-10)

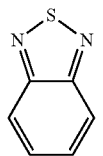 (3-11)

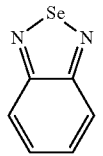 (3-12)

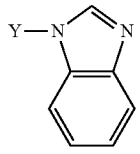 (3-13)

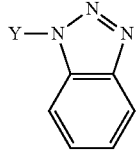 (3-14)

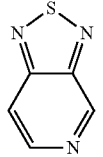 (3-15)

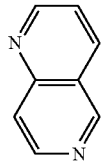 (3-16)

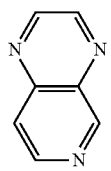 (3-17)

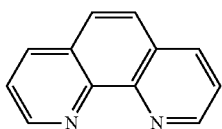 (3-18)

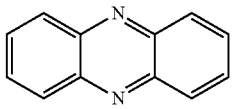 (3-19)

In Chemical Formula 3, Y is hydrogen, a C1 to C20 linear or branched alkyl group, a C3 to C20 cycloalkyl group, a C6 to C30 aryl group, a C1 to C16 linear or branched alkoxy group, or a C3 to C16 cycloalkoxyalkyl group. The binding site of the substituent of Chemical Formula 3 to Chemical Formula 1 is not specifically limited, so it is not illustrated, separately.

The C2 to C30 heteroaromatic ring group including at least one electron withdrawing imine nitrogen atom may include a thiazolyl group, a thiadiazolyl group, an isoxazolyl group, an oxadiazolyl group, an imidazolyl group, a pyrazolyl group, a trizolyl group, tetrazolyl group, a pyridyl group, a pyridazinyl group, a quinolinyl group, an isoquinolinyl group, a quinoxalinyl group, a naphthyridinyl group, a benzoimidazolyl group, a pyrimidopyrimidinyl group, a benzothiadiazolyl group, a benzoselenadiazolyl group, a benzotriazolyl group, a benzothiazolyl group, a benzoxazolyl group, a phenanthrolinyl group, a phenazinyl group, a phenanthridinyl group, and the like.

The C2 to C30 heteroaromatic ring group including at least one sulfur atom may be selected from the groups represented by the following Chemical Formula 4.

[Chemical Formula 4]

 (4-1)

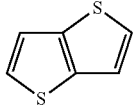 (4-2)

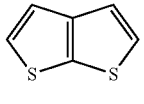 (4-3)

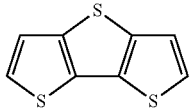 (4-4)

-continued (4-5)

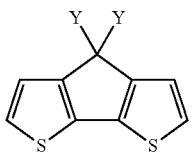

In Chemical Formula 4,

Y is hydrogen, a C1 to C20 linear or branched alkyl group, a C3 to C20 cycloalkyl group, a C6 to C30 aryl group, a C1 to C16 linear or branched alkoxy group, or a C3 to C16 cycloalkoxyalkyl group. Y may be in plural, and a plurality of Y may be the same or different. The binding site of the substituent of Chemical Formula 4 to Chemical Formula 1 is not specifically limited, so it is not illustrated, separately.

According to another example embodiment, an organic semiconductor polymer including a structural unit represented by the following Chemical Formula 5 is provided.

[Chemical Formula 5]

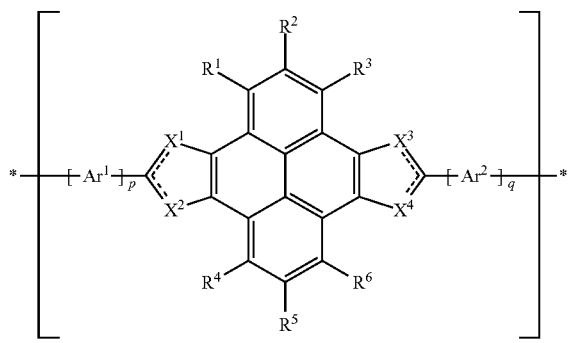

In Chemical Formula 5, $X^1$ to $X^4$ and $R^1$ to $R^6$ are the same as in Chemical Formula 1, and $Ar^1$ and $Ar^2$ are each independently substituted or unsubstituted C6 to C30 aromatic ring group, a substituted or unsubstituted C4 to C14 heteroaromatic ring group, or a substituted or unsubstituted C6 to C30 condensed polycyclic group, p and q are each independently integers ranging from 0 to 10, or about 1 to 10, and when p or q are each 2 or more, a plurality of $Ar^1$ and $Ar^2$ are the same or different from each other. The sum of p and q may be 2 or more.

In Chemical Formula 5, the $Ar^1$ structural unit, pyrene derivative structural unit, and $Ar^2$ structural unit may be alternately arranged, or randomly arranged each other.

The organic semiconductor polymer including the structural unit represented by Chemical Formula 5 may be an organic semiconductor polymer including a structural unit represented by the following Chemical Formula 6.

[Chemical Formula 6]

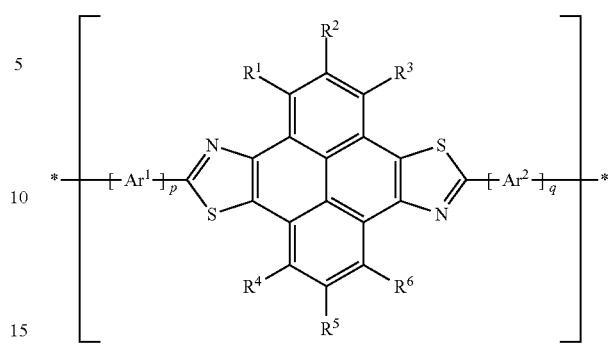

In Chemical Formula 6, $R^1$ to $R^6$ may be the same as in Chemical Formula 1, and $Ar^1$ and $Ar^2$ may be the same as in Chemical Formula 5.

In Chemical Formula 6, the $Ar^1$ structural unit, pyrene derivative structural unit, and $Ar^2$ structural unit may be alternately arranged, or randomly arranged.

The $Ar^1$ and $Ar^2$ may include at least one thiophenyl group, and may be represented by the following Chemical Formula 7.

[Chemical Formula 7]

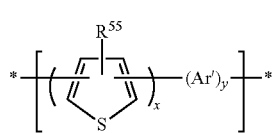

In Chemical Formula 7, $R^{55}$ is selected from hydrogen, or a C1 to C20 alkyl group, Ar' is selected from a C6 to C30 arylene group, a C6 to C30 condensed polycyclic group, C2 to C30 heteroaromatic ring group, C2 to C30 heteroaromatic ring group including at least one electron withdrawing imine nitrogen atom, a C2 to C30 heteroaromatic ring group including at least one sulfur atom, or combination thereof, x is an integer ranging from 1 to 7, and y is an integer ranging from 0 to 4, or about 1 to 4. In Chemical Formula 7, the thiophenyl structural unit and Ar' structural unit may be alternately arranged, or randomly arranged each other. Specific examples of the C2 to C30 heteroaromatic ring group including at least one electron withdrawing imine nitrogen atom, a C2 to C30 heteroaromatic ring group including at least one sulfur atom may be the same as described above.

The $Ar^1$ and $Ar^2$ may be selected from a substituted or unsubstituted phenylene group, a substituted or unsubstituted thiophene group, a substituted or unsubstituted benzothiophene group, a substituted or unsubstituted thienothiophene group, a substituted or unsubstituted thiazole group, a substituted or unsubstituted thiazolothiazole group, a substituted or unsubstituted fluorene group, a substituted or unsubstituted carbazole group, and a combination thereof.

The organic semiconductor polymer including the structural unit represented by Chemical Formula 5 may include one of the compounds represented by the following Chemical Formulae 8-1 to 8-4.

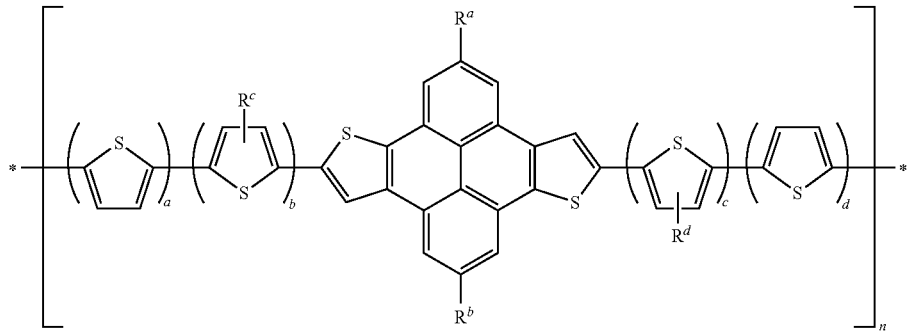

[Chemical Formula 8-1]

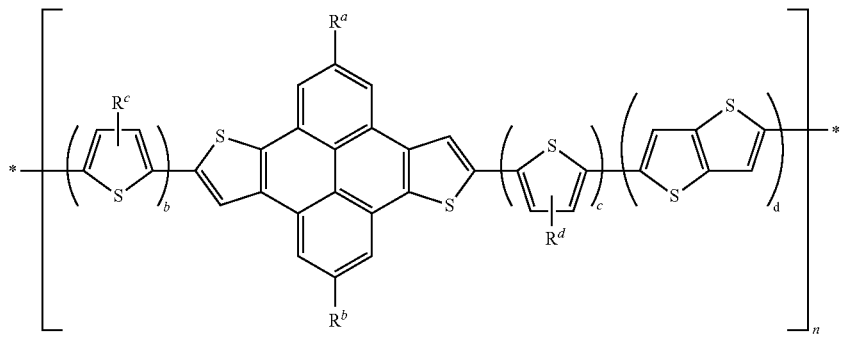

[Chemical Formula 8-2]

In Chemical Formulae 8-1 and 8-2, $R^a$ and $R^b$ are a C1 to C10 alkyl group or a C2 to C30 heteroaromatic ring group including at least one electron withdrawing imine nitrogen atom, or $R^a$ or $R^b$ may form a thiophenyl ring group or a thiazolyl ring group fused with a pyrene moiety, provided that at least one of $R^a$ and $R^b$ is a C2 to C30 heteroaromatic ring group including at least one electron withdrawing imine nitrogen atom, or $R^a$ or $R^b$ forms a thiophenyl ring group or a thiazolyl ring group fused with a pyrene moiety, $R^c$ and $R^d$ is a C1 to C20 alkyl group such as a dodecyl group, a, b, c, and d are integers ranging from 0 to 10, or about 1 to 10, and a+b and c+d are 10 or less, and n is a polymerization degree of a polymer. In addition, $R^c$ and $R^d$ may be disposed in symmetrical to each other in the center of thiophenyl ring group fused with the pyrene moiety.

[Chemical Formula 8-3]

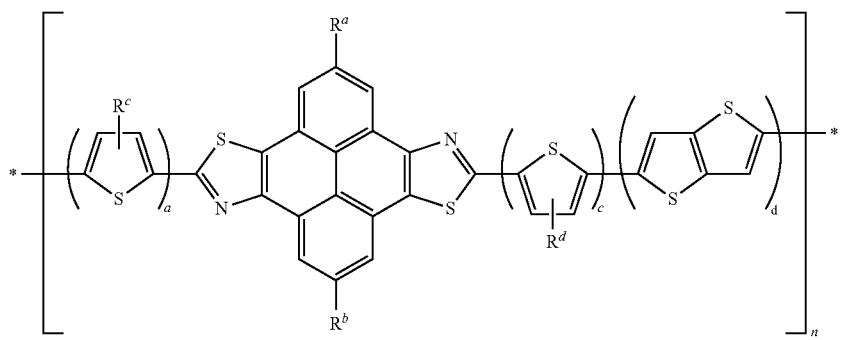

[Chemical Formula 8-4]

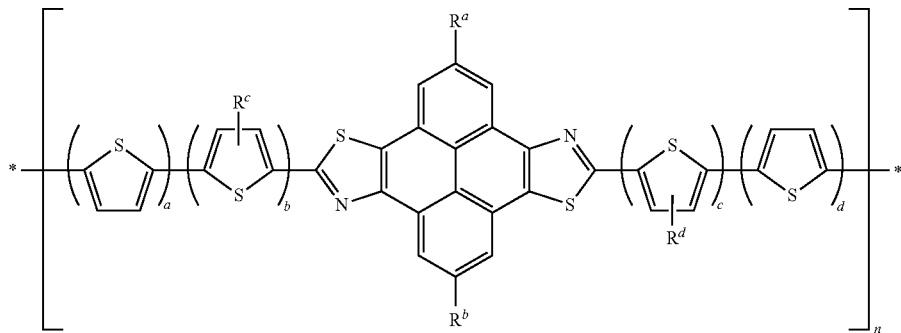

In Chemical Formulae 8-3 and 8-4, $R^a$ and $R^b$ are a C1 to C10 alkyl group such as a t-butyl group or a C2 to C30 heteroaromatic ring group including at least one electron withdrawing imine nitrogen atom, or $R^a$ or $R^b$ may form a thiophenyl ring group or a thiazolyl ring group fused with a pyrene moiety, $R^c$ and $R^d$ are a C1 to C20 alkyl group such as a dodecyl group, a, b, c, and d are integers ranging from 0 to 10, or about 1 to 10, and a+b and c+d are 10 or less, and n is a polymerization degree of a polymer. In addition, $R^c$ and $R^d$ may be disposed in symmetrical to each other in the center of thiazolyl ring group fused with the pyrene moiety.

In Chemical Formulae 8-1 and 8-2, at least one of $R^a$ and $R^b$ may be represented by the following Chemical Formula 9-1 to the following Chemical Formula 9-4 in the case of a C2 to C30 heteroaromatic ring group including at least one electron withdrawing imine nitrogen atom; and it may be represented by the following Chemical Formula 9-5 or the following Chemical Formula 9-6 in the case that $R^a$ or $R^b$ forms a thiazolyl ring group fused with the pyrene moiety.

[Chemical Formula 9-1]

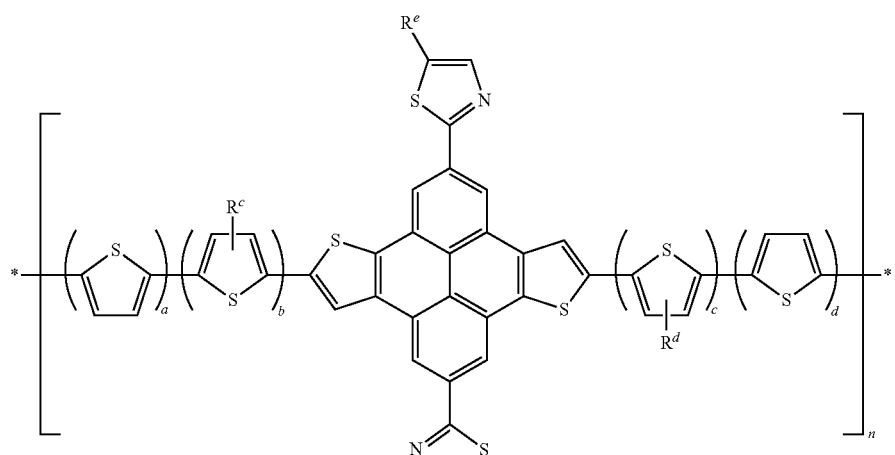

[Chemical Formula 9-2]

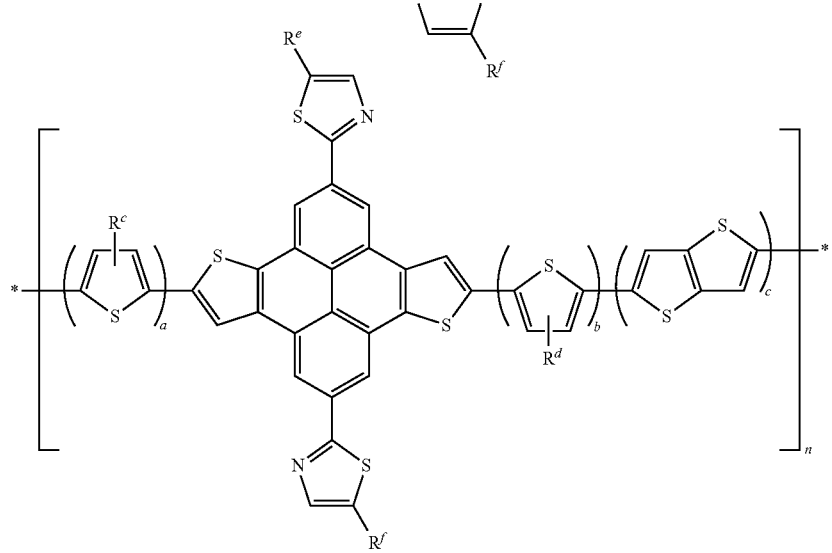

[Chemical Formula 9-3]
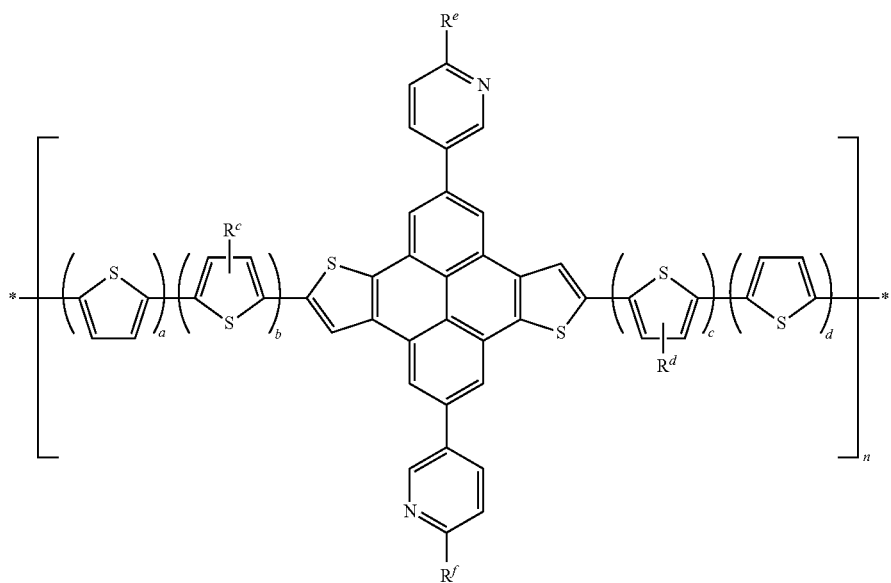
[Chemical Formula 9-4]
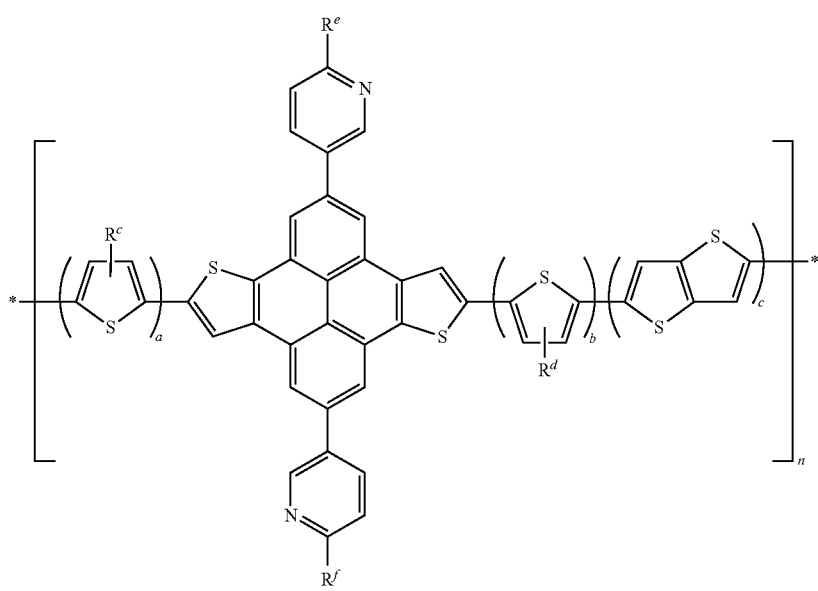

[Chemical Formula 9-5]

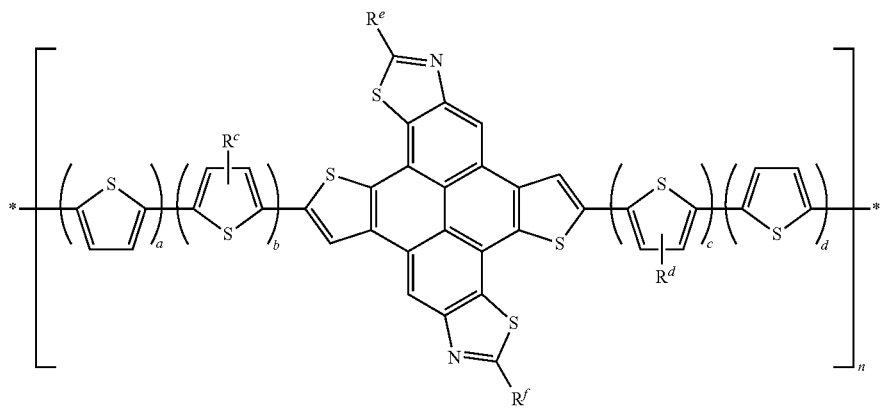

[Chemical Formula 9-6]

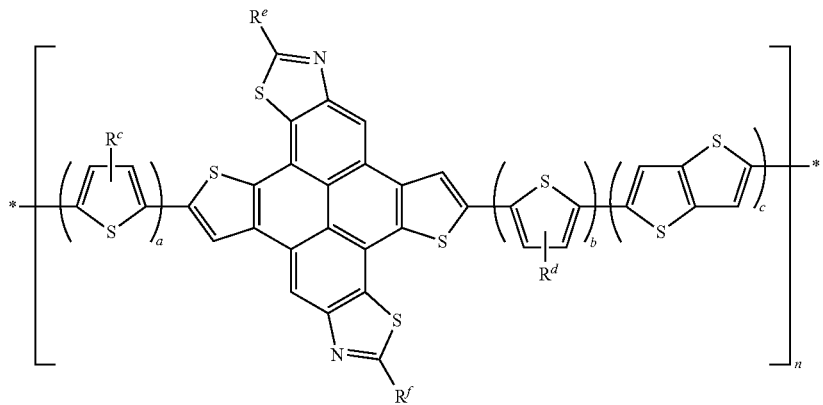

In Chemical Formulae 9-1 to 9-6, $R^c$, $R^d$, a, b, c, d, and n may be the same as in Chemical Formulae 8-1 and 8-2, and $R^e$ or $R^f$ is a C1 to C20 alkyl group such as a dodecyl group.

The organic semiconductor polymer may have a number average molecular weight (Mn) of about 5000 to about 200,000, specifically about 10,000 to about 100,000, and more specifically about 10,000 to about 50,000. When the number average molecular weight ranges within the above range, a solution process such as inkjet printing or drop-casting may be performed easily.

The organic semiconductor compound or polymer may be a p-type organic semiconductor compound or organic semiconductor polymer.

The organic semiconductor polymer including a structural unit of the above Chemical Formula 5 may be synthesized according to methods disclosed in Stille et al. (Angew. Chem. Int. Ed. Engl. 1986, Vol. 25, pp. 508-524), Suzuki et al. (J. Am. Chem. Soc. 1989, Vol. 111, pp. 314-321), McCullough et al. (U.S. Pat. No. 6,166,172, 1999), or Yamamoto et al. (Macromolecules 1992, Vol. 25, pp. 1214-1226). For example, the organic semiconductor polymer including structural unit of Chemical Formula 5 may be synthesized by reacting monomers as shown in the following Reaction Scheme 1.

[Reaction Scheme 1]

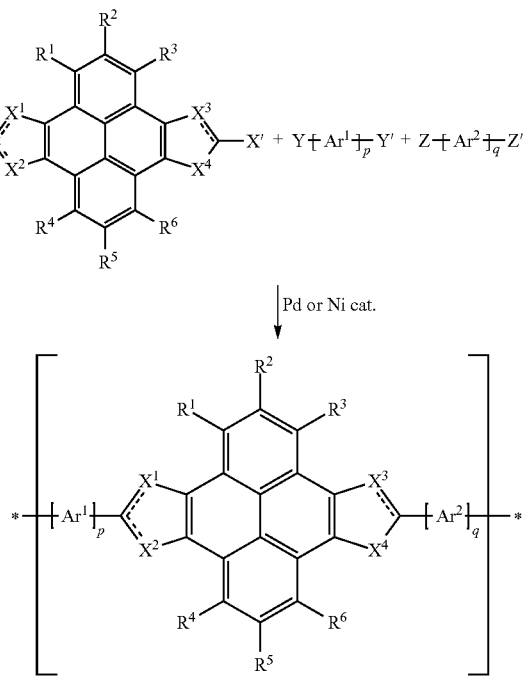

In Reaction Scheme 1, $X^1$ to $X^4$, $R^1$ to $R^8$, $Ar^1$ and $Ar^2$, p, and q may be the same as in Chemical Formula 5, X, X', Y, Y', Z, and Z' are each independently a reactive group selected from a halogen such as Br, I, Cl, and the like, a trialkyltin group and a boron-containing group, but are not limited thereto.

The trialkyltin group may be represented by the following Chemical Formula 10, and the boron-containing group may be represented by the following Chemical Formula 11 or 12.

[Chemical Formula 10]

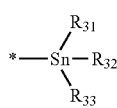

In the above Chemical Formula 10, $R_{31}$ to $R_{33}$ are the same or different and are independently hydrogen or a C1 to C7 alkyl, provided that at least one of $R_{31}$ to $R_{33}$ is an alkyl.

[Chemical Formula 11]

[Chemical Formula 12]

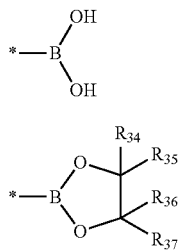

In Chemical Formula 12, $R_{34}$ to $R_{37}$ are the same or different and are independently hydrogen or a C1 to C7 alkyl, provided that at least one of $R_{34}$ to $R_{37}$ is an alkyl.

A catalyst may be used in the reaction of the Reaction Scheme 1, and may be an organic metal catalyst represented by the following Chemical Formulae 13-1 to 13-4.

$Pd(L_1)_x$      [Chemical Formula 13-1]

$Pd(L_2)_{4-y}Cl_y$      [Chemical Formula 13-2]

In the above Chemical Formulae 13-1 and 13-2, $L_1$ and $L_2$ are ligands selected from triphenylphosphine ($PPh_3$), 1,4-bis(diphenylphosphino)butane (dppb), 1,1'-bis(diphenylphosphino)ferrocene (dppf), acetate (OAc), triphenyl arsine ($AsPh_3$), and triphenylphosphite ($P(OPh)_3$), x is an integer ranging from 2 to 4, and y is an integer ranging from 1 to 3.

$Ni(L_3)_x$      [Chemical Formula 13-3]

$Ni(L_4)_{3-y}Cl_y$      [Chemical Formula 13-4]

In Chemical Formulae 13-3 and 13-4, $L_3$ and $L_4$ are ligands selected from the group consisting of a diphenylphosphinoalkane such as 1,3-bis(diphenylphosphino)propane (dppp), 1,2-bis(diphenylphosphino)ethane (dppe), 1,4-bis(diphenylphosphino)butane (dppb), and the like, and a cycloalkene such as bis(1,5-cyclooctadiene) (COD), and the like, x is an integer of 2 or 3, and y is an integer of 1 or 2.

Examples of palladium catalysts include a palladium (0) catalyst such as a tetrakis(triphenylphosphine)palladium (0) compound ($Pd(PPh_3)_4$), and palladium (II) catalysts such as 1,4-bis(triphenylphosphine)palladium(II)dichloride ($PdCl_2P(Ph_3)_2$), [1,4-bis(diphenylphosphino)butane]palladium (II) dichloride ($Pd(dppb)Cl_2$), [1,1'-bis(diphenylphosphino)ferrocene]palladium (II)dichloride ($Pd(dppf)Cl_2$), palladium (II)acetate ($Pd(OAc)_2$), and the like.

Examples of nickel catalysts include a nickel (0) catalyst such as a bis(1,5-cyclooctadiene)nickel (0) compound ($Ni(COD)_2$), and a nickel (II) catalyst such as 1,3-bis(diphenylphosphino)propane nickel (II)dichloride ($Ni(dppp)Cl_2$), 1,2-bis(diphenylphosphino)ethane nickel (II)dichloride ($Ni(dppe)Cl_2$), and the like.

The catalyst may be used by adjusting its amount according to amounts of the monomers. For example, the tetrakis (triphenylphosphine) palladium (0) compound may be used at about 0.2 to about 15 mol % with respect to monomers, and in one embodiment, it may be used at about 2 to about 10 mol % with respect to monomers.

A polymerization solvent such as toluene, dimethylformamide (DMF), tetrahydrofuran (THF), N-methylpyrrolidinone (NMP), and the like may be used.

Polymerization reaction may be performed at about 80 to about 120° C. for about 6 to about 48 hours under a nitrogen atmosphere.

The organic semiconductor polymer is applicable to an active layer of a transistor. The transistor includes a gate electrode positioned on a substrate, a source electrode and a drain electrode facing each other and defining a channel region, an insulation layer that electrically insulates the source electrode and drain electrode, and the gate electrode, and an active layer including the organic semiconductor polymer in the channel region. The organic semiconductor compound of Chemical Formula 1 may be also included in the channel region.

The active layer may be prepared by a solution process of a composition including an organic semiconductor compound or polymer such as screen printing, printing, spin coating, dipping, inkjetting, and so on. When the active layer is obtained by a solution process, the process cost may be reduced, and it is useful for fabricating a large area device.

Figure 2:
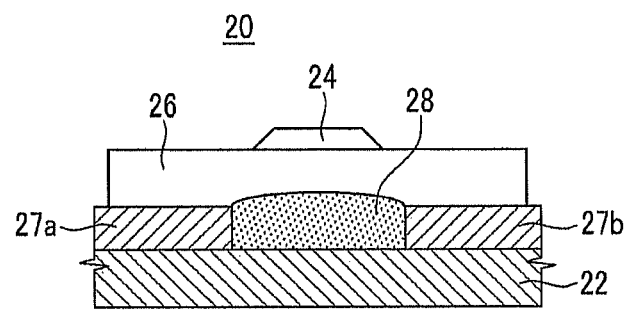
FIG. 2 is a schematic cross-sectional view of a transistor according to another example embodiment.

FIGS. 1 and 2 are schematic cross-sectional views showing a transistor according to an example embodiment. The transistor according to an example embodiment may be a thin film transistor. The thin film transistor may be a thin film having a thickness of several nm to several μm.

Referring to FIG. 1, a transistor 10 includes a substrate 12, a gate electrode 14 disposed on the substrate, and an insulation layer 16 covering the gate electrode 14. On the insulation layer 16, a source electrode 17a and a drain electrode 17b defining a channel region are provided, and an active layer 18 is provided in the channel region. The active layer 18 includes an organic semiconductor polymer.

Referring to FIG. 2, in a transistor 20, a source electrode 27a and a drain electrode 27b defining a channel region are formed on a substrate 22, and an active layer 28 is formed on the channel region. The active layer 28 includes an organic semiconductor polymer. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic such as polyethylenenaphthalate (PEN), polyethyleneterephthalate (PET), polycarbonate, polyvinylalcohol, polyacrylate, polyimide, polynorbornene, and polyethersulfone (PES), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but it is not limited thereto.

The insulation layers 16 and 26 may include: a generally-used insulator having a high dielectric constant, particularly a ferroelectric insulator such as $Ba_{0.33}Sr_{0.66}TiO_3$ (BST, barium strontium titanate), $Al_2O_3$, $Ta_2O_5$, $La_2O_5$, $Y_2O_3$, $TiO_2$; an inorganic insulator such as $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$(BZT), $BaTiO_3$, $SrTiO_3$, $SiO_2$, $SiN_x$, AlON and so on; or an organic insulator such as polyimide, benzocyclobutene (BCB), parylene, polyacrylate, polyvinylalcohol, polyvinylphenol, and so on, but it is not limited thereto. Although it is not mentioned above, the inorganic insulator disclosed in U.S. Pat. No. 5,946,551 and the organic insulator disclosed in U.S. Pat. No. 6,232,157 may be used for the insulation layers 16 and 26.

The organic semiconductor polymer is applicable for solar cell, a memory device, an organic light emitting diode (OLED), a photosensor, a laser device, and so on.

Hereinafter, some non-limiting example embodiments are illustrated in more detail.

EXAMPLES

Example 1

An organic semiconductor compound and an organic semiconductor polymer are synthesized according to the following Reaction Scheme 2.

[Reaction Scheme 2]

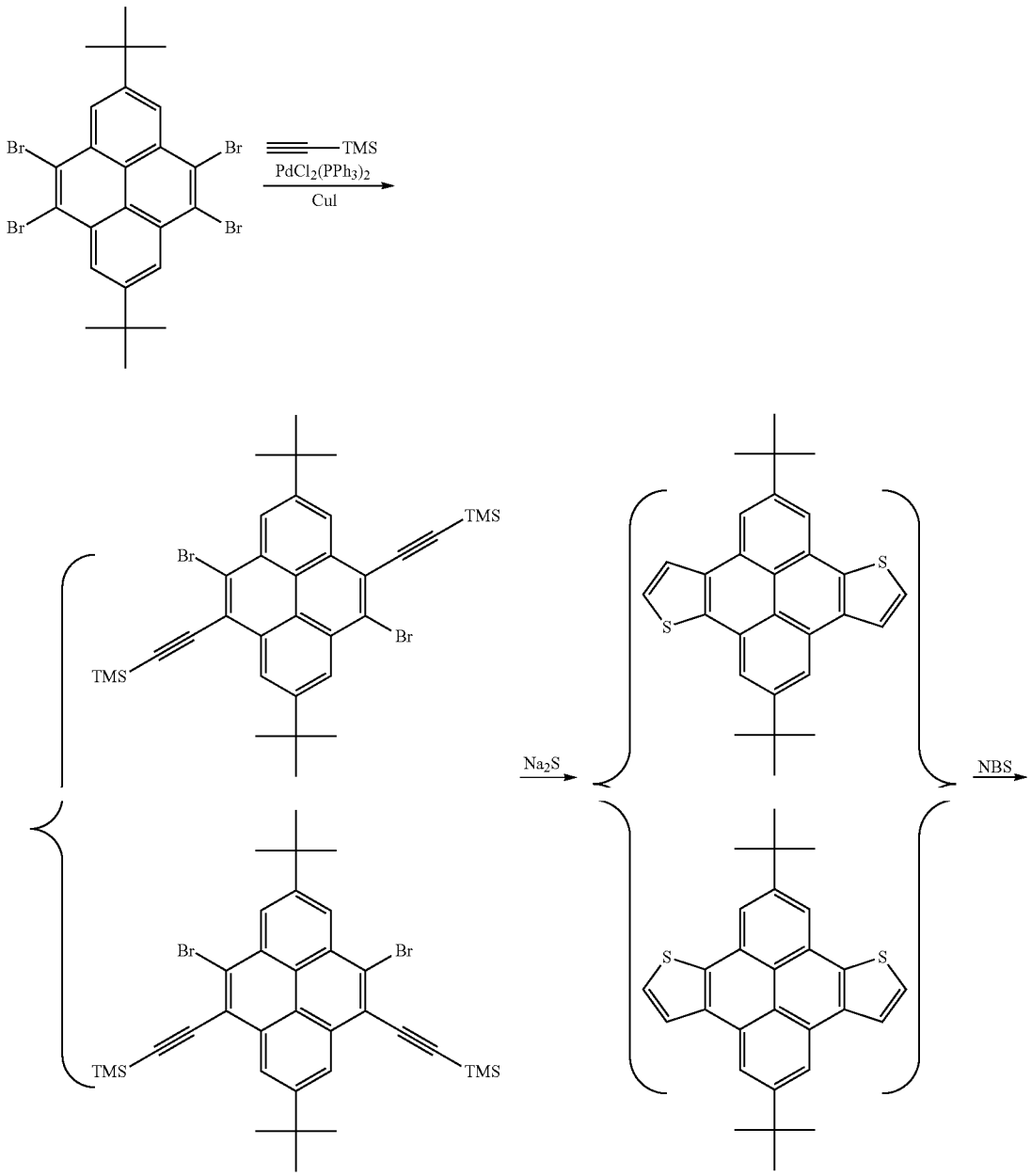

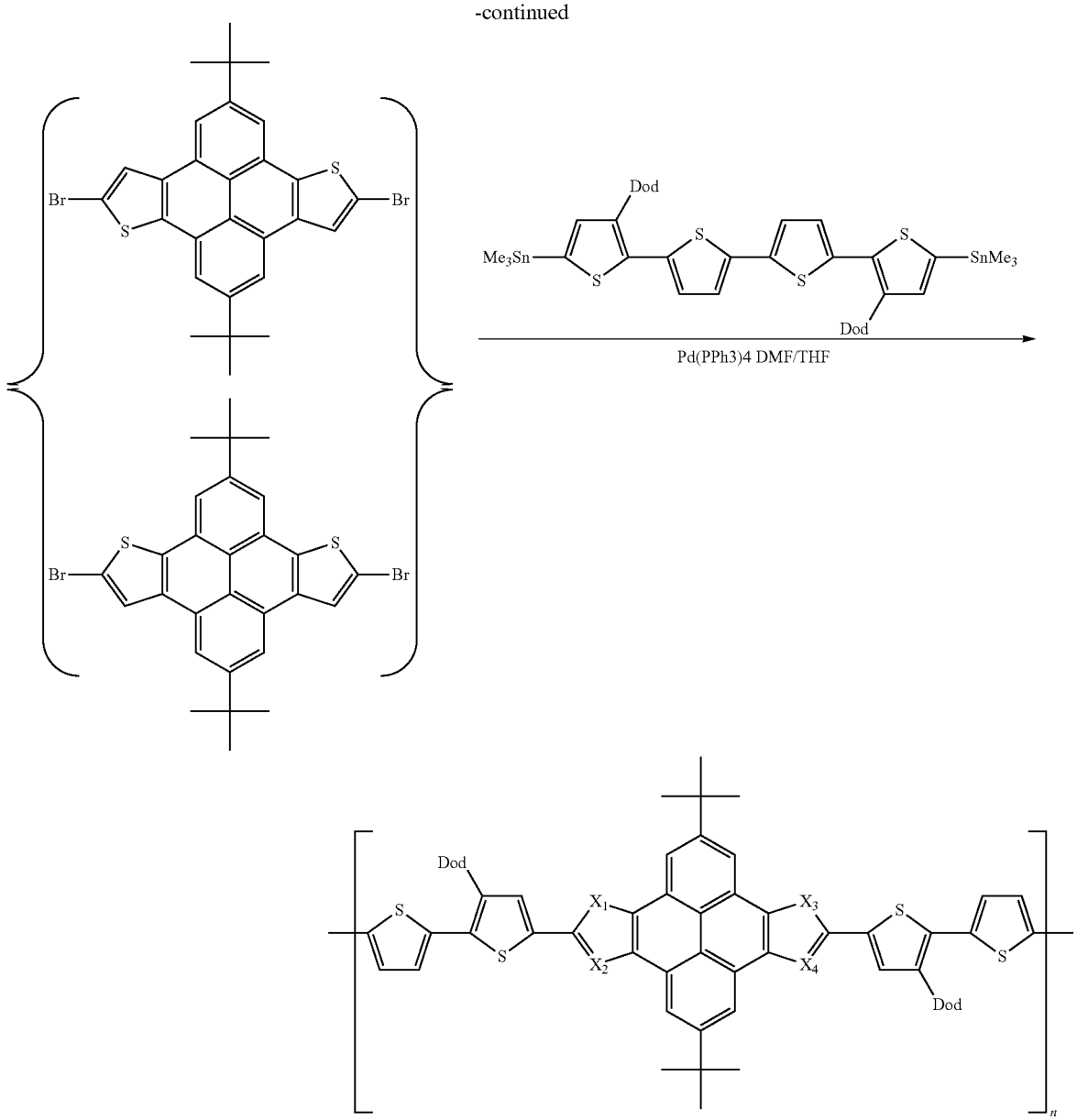

either X1 or X2 is S and the other is CH, and
either X3 or X4 is S and the other is CH.

Example 1-1

Synthesis of 2,7-di-tert-butyl-5,10-dibromo-4,9-di(trimethylsilylethynyl)pyrene and 2,7-di-tert-butyl-4,10-dibromo-5,9-di(trimethylsilylethynyl)pyrene 2,7-di-tert-butyl-4,5,9,10-tetrabromopyrene (1 mmol) and copper (I) iodide (40 mg), trimethylsilylacetylene (3 mmol), triethylamine (2 ml), and Pd(PPh$_3$)$_2$Cl$_2$ (0.02 mmol) are mixed in THF (3 ml) and agitated at 60° C. overnight. A solid is filtered by a silica pad, and a solution is dried under a reduced pressure to be separated through a column chromatography (hexane).

$^1$H NMR (300 MHz, CDCl$_3$): δ (ppm) 8.85-8.78 (dd, 4H), 1.61 (m, 18H), 0.43 (m, 18H). Maldi-MS Calcd for C$_{34}$H$_{40}$Br$_2$Si$_2$: 662.1035. Found: 662.104.

Example 1-2

Synthesis of 2,7-di-tert-butyl-pyreno[4,5-b:9,10-b']dithiophene and 2,7-di-tert-butyl-pyreno[4,5-b:9,10-b]dithiophene A mixture (200 mg) of 2,7-di-tert-butyl-5,10-dibromo-4,9-di(trimethylsilylethynyl)pyrene and 2,7-di-tert-butyl-4,10-dibromo-5,9-di(trimethylsilylethynyl)pyrene are dissolved in N-methylmorpholine (1 ml) and 1 g of Na$_2$S.9H$_2$O is added thereto, and agitated at 185° C. for 12 hours. The black-changed reaction mixture is cooled until room temperature (24° C.) and separated into water and chloroform layers. The organic layer is dried under a reduced pressure and separated through a columnchromatography (hexane).

¹H NMR (300 MHz, CDCl₃): δ (ppm) 8.60 (s, 1H), 8.58 (d, 1H), 8.40 (d, 1H), 8.38 (s, 1H), 8.20-8.17 (m, 2H), 7.68-7.66 (m, 2H), 1.64 (m, 18H).

Example 1-3

Figure 3:
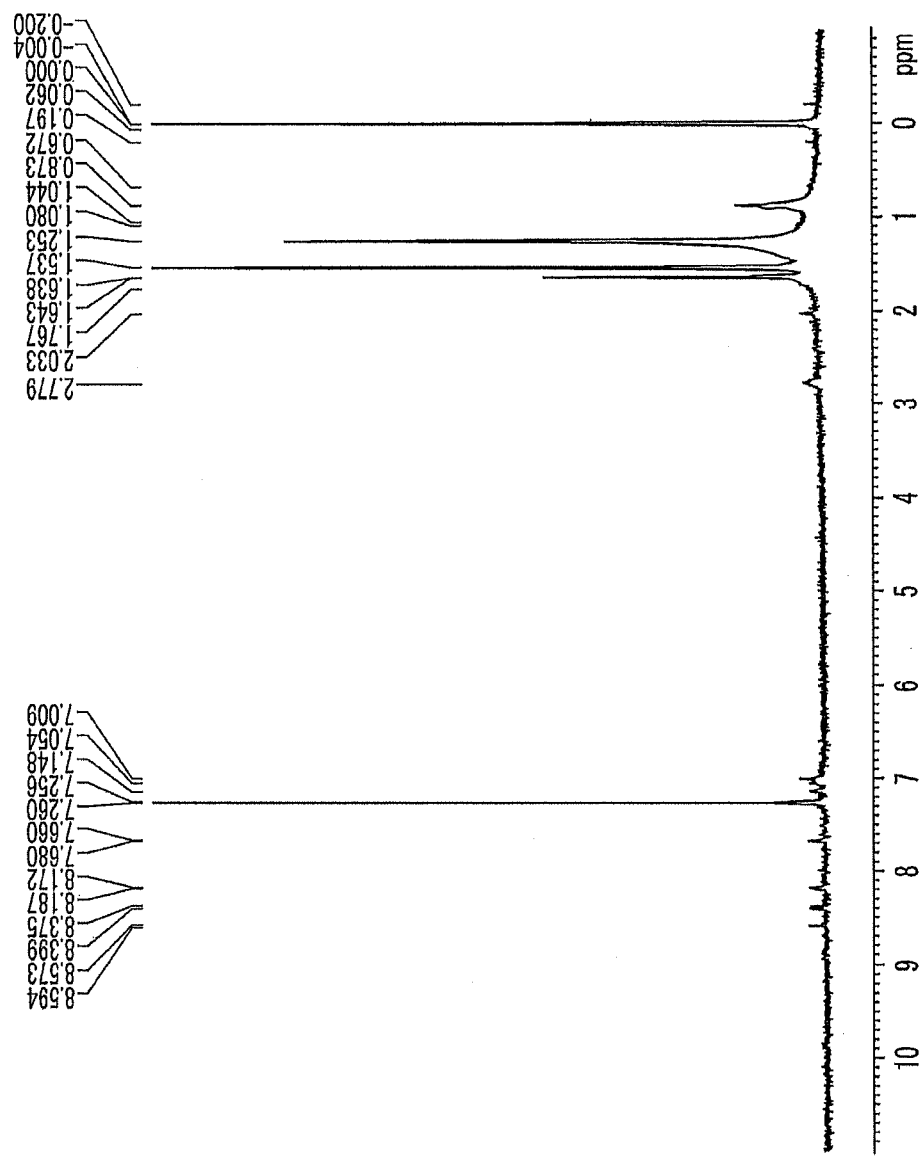
FIG. 3 shows $^1$H NMR analysis result of the organic semiconductor polymer according to Example 1.

Synthesis of polymer (PPDTQT) including 2,7-di-tert-butyl-pyreno[4,5-b:9,10-b']dithiophene and 2,7-di-tert-butyl-pyreno[4,5-b:9,10-b]dithiophene A mixture of 2,7-di-tert-butyl-pyreno[4,5-b:9,10-b']dithiophene and 2,7-di-tert-butyl-pyreno[4,5-b:9,10-b]dithiophene is reacted with N-bromosuccinimide (NBS) (2 eq.) to provide a dibromo compound and performed with a Stille coupling reaction by using 5,5'''-di(trimethylstannyl)-3,3'''-di(dodecyl)quarterthiophene (1.0 eq.) and Pd(PPh₃)₄ catalyst (0.1 eq.) to provide a polymer (PPDTQT). ¹H NMR of the obtained polymer is shown in FIG. 3. The polymer has a number average molecular weight (Mn) of about 13 k.

Example 2

An organic semiconductor compound and an organic semiconductor polymer are synthesized according to the following reaction scheme 3.

[Reaction Scheme 3]

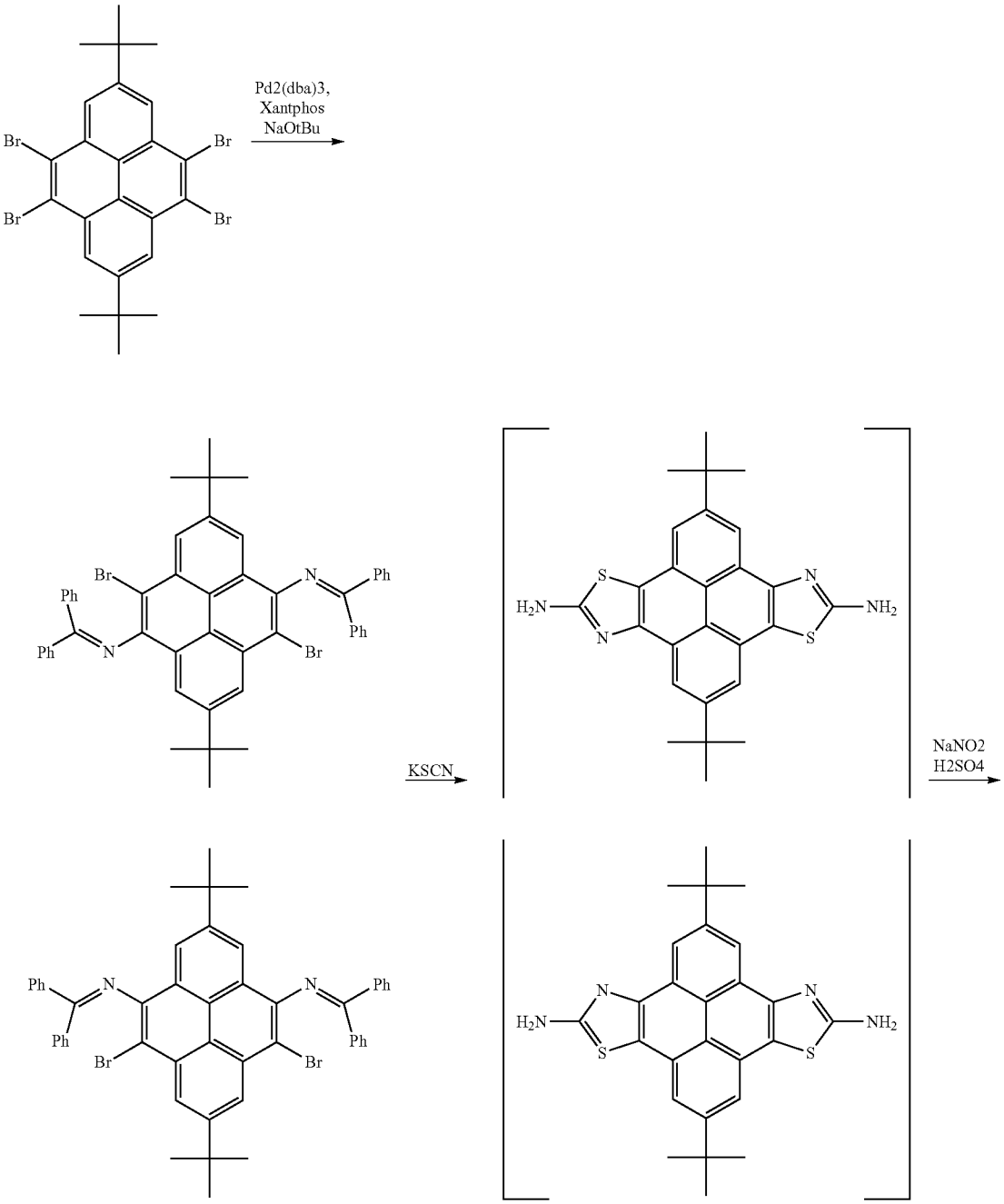

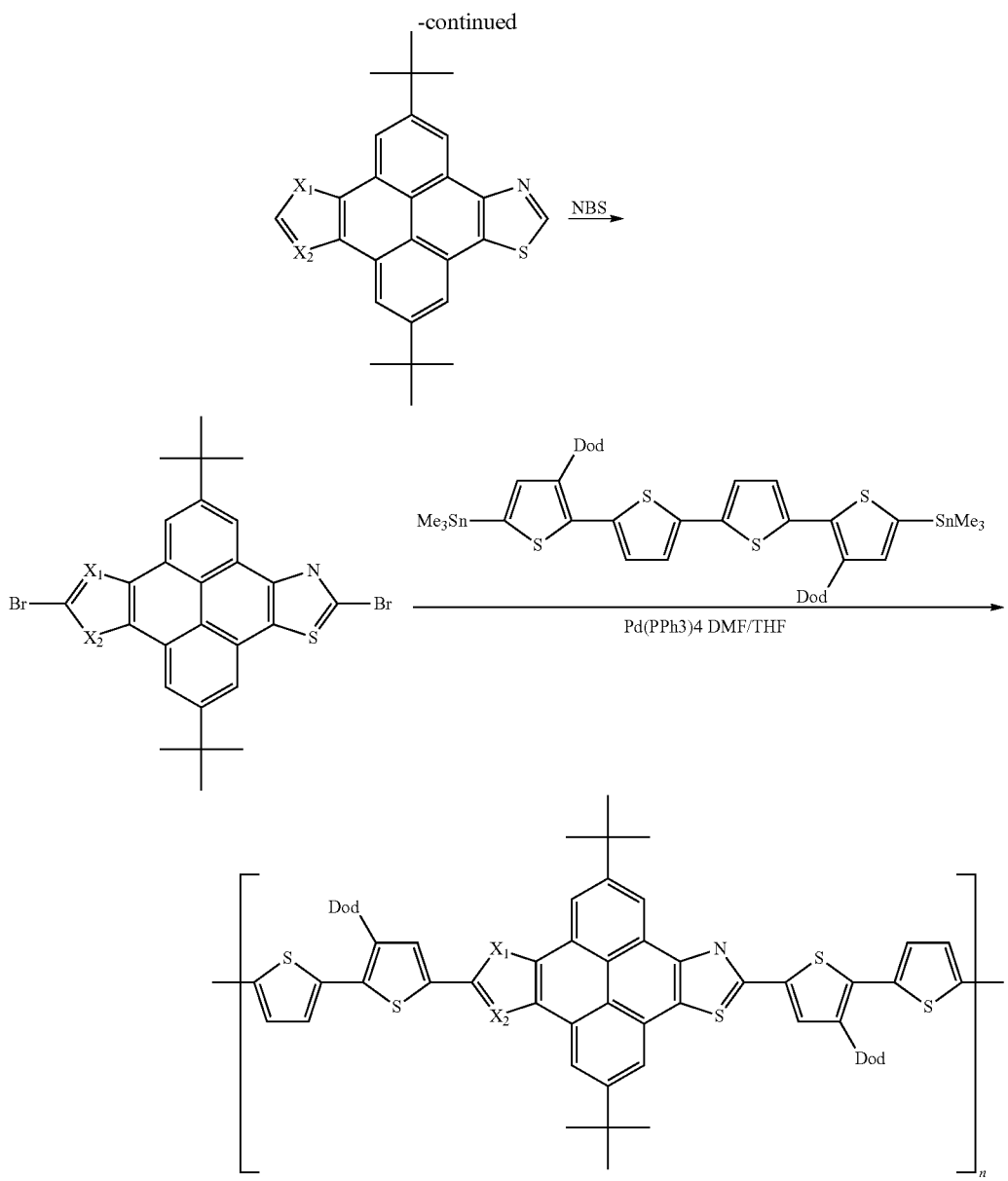

either X1 or X2 is S and the other is N.

Example 2-1

Synthesis of 2,7-di-tert-butyl-5,10-dibromo-4,9-di(diphenylmethyleneamino)pyrene and 2,7-di-tert-butyl-4,10-dibromo-5,9-di(diphenylmethyleneamino)pyrene 2,7-di-tert-butyl-4,5,9,10-tetrabromopyrene (10 mmol) is dissolved in 20 ml of toluene and $Pd_2(dba)_3$ (0.4 mmol), Xantphos (0.8 mmol), and NaO-t-Bu (50 mmol) are added thereto. The resultant is agitated at room temperature (24° C.) for 30 minutes, and diphenylmethanimine (23 mmol) is added and then the resultant is agitated at 100° C. for 24 hours. The reaction mixture is cooled until room temperature (24° C.) and filtered using a silica pad and concentrated under a reduced pressure. The resultant is separated through the chromatography (hexane:chloroform=3:1 volume ratio).

$^1$H NMR (300 MHz, $CDCl_3$): δ (ppm) 8.51 (d, 2H), 8.09 d, 2H), 7.99 (br, 4H), 7.54 (m, 8H), 7.22 (m, 4H), 7.04 (m, 4H), 1.49 (t, 18H). Maldi-MS Calcd for $C_{50}H_{42}Br_2N_2$: 828.17. Found: 828.17.

Example 2-2

Synthesis of 2,7-di-tert-butyl-pyreno[4,5-b:9,10-b']dithiazole and 2,7-di-tert-butyl-pyreno[4,5-b:9,10-b]dithiazole A mixture (1 mmol) of 2,7-di-tert-butyl-5,10-dibromo-4,9-di(diphenylmethyleneamino)pyrene and 2,7-di-tert-butyl-4,10-dibromo-5,9-di(diphenylmethyleneamino)pyrene is dissolved in 10 ml of acetic acid and 10 ml of chloroform and potassium thiocyanate (KSCN) (10 mmol) is added thereto and agitated at room temperature (24° C.) for 48 hours. It is filtered to provide an orange solid. The solid is slowly added into a solution that sulfuric acid (1 ml), 95% ethanol (5 ml), and NaNO$_2$ (1 g) are dissolved at 0° C. After agitating for one hour, it is heated for one hour to agitate and refluxe and cooled until room temperature (24° C.) and poured into a cold water to provide a precipitate. The precipitate is filtered to provide an orange solid.

$^1$H NMR (300 MHz, CDCl$_3$): δ (ppm) 8.69 (m, 2H), 8.52 (m, 2H), 8.46 (m, 2H), 1.65 (t, 18H).

Example 2-3

Figure 4:
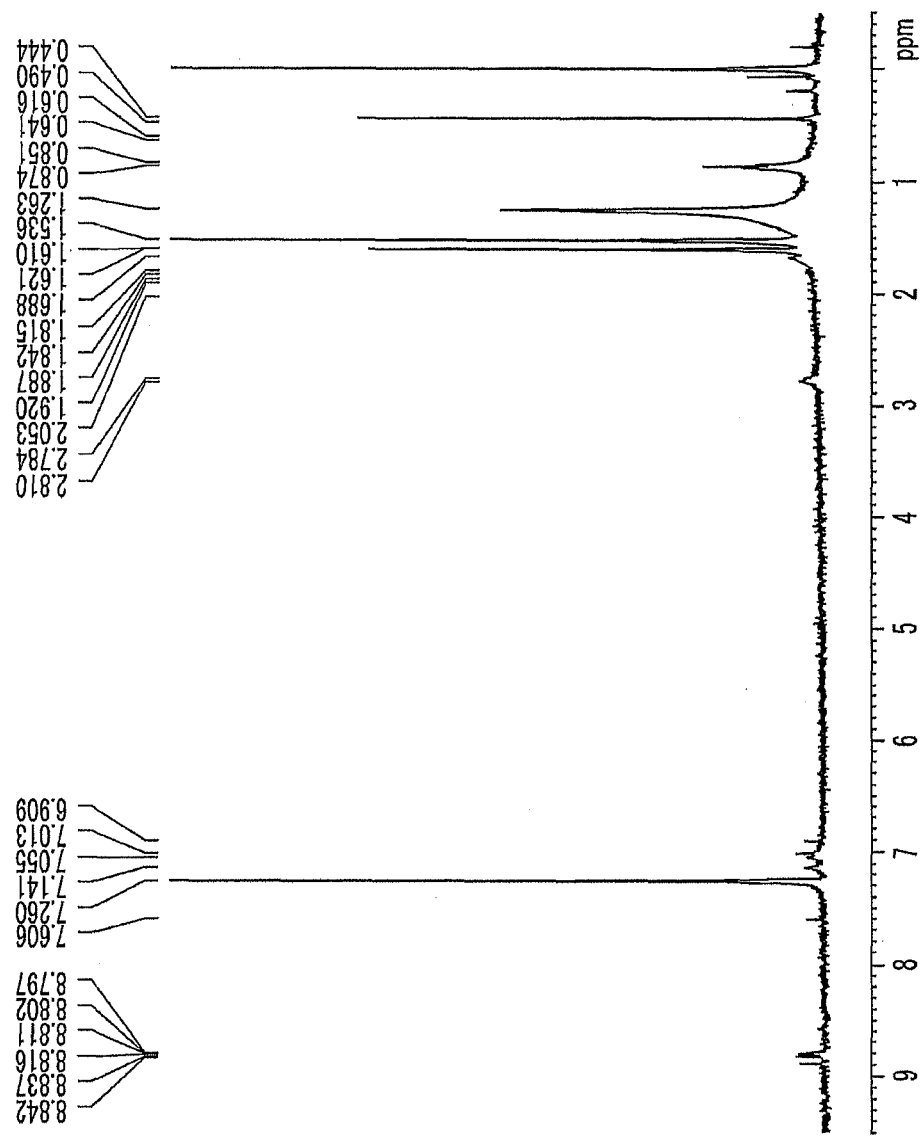
FIG. 4 shows $^1$H NMR analysis result of the organic semiconductor polymer according to Example 2.

Synthesis of polymer including 2,7-di-tert-butyl-pyreno[4,5-b:9,10-b']dithiazole and 2,7-di-tert-butyl-pyreno[4,5-b:9,10-b]dithiazole A mixture (0.2 mmol) of 2,7-di-tert-butyl-pyreno[4,5-b:9,10-b']dithiazole and 2,7-di-tert-butyl-pyreno[4,5-b:9,10-b]dithiazole is reacted with NBS (2 eq.) to provide a dibromo compound and performed with a Stille coupling reaction using 5,5'''-di(trimethylstannyl)-3,3'''-di(dodecyl) quarterthiophene (1.0 eq.) and Pd(PPh$_3$)$_4$ catalyst (0.1 eq.) to provide a polymer (PPDTZQT). $^1$H NMR of the obtained polymer is shown in FIG. 4. The polymer has a number average molecular weight (Mn) of 15 k.

Example 3

An organic semiconductor compound is synthesized according to the following reaction scheme 4.

[Reaction Scheme 4]

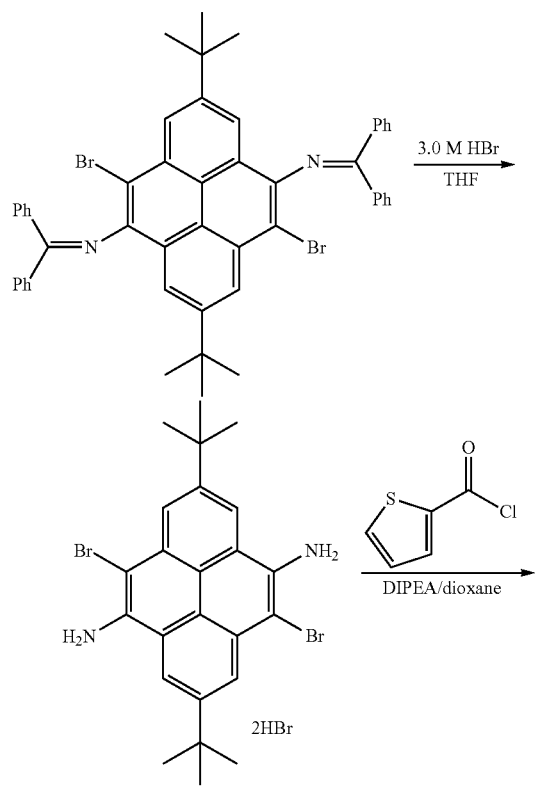

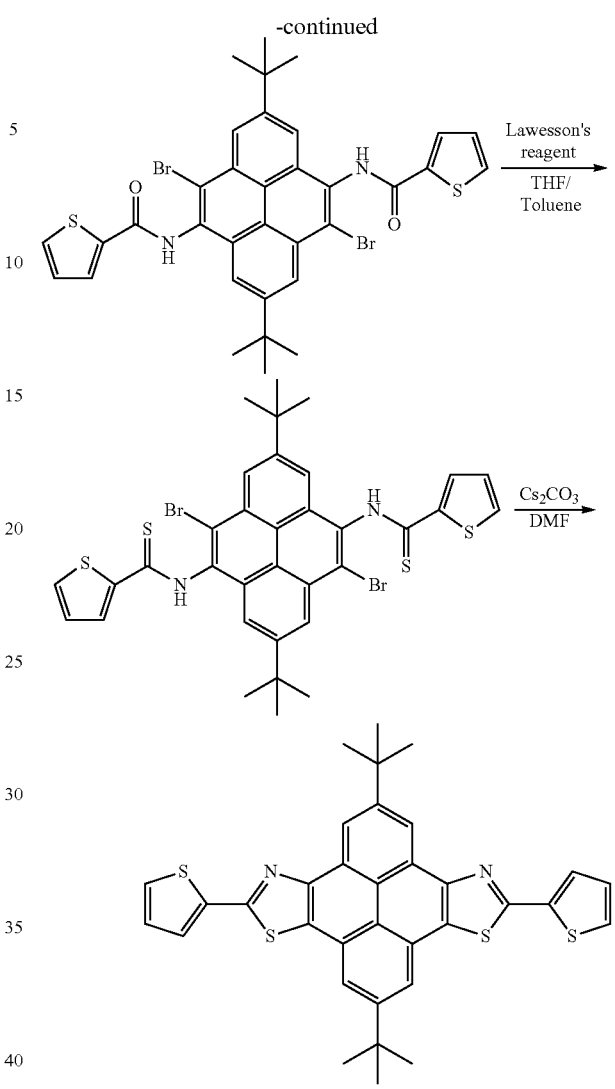

Example 3-1

Synthesis of 5,10-dibromo-2,7-di-tert-butylpyrene-4,9-diamine

3N HBr solution is added to a stirred solution of 5,10-dibromo-2,7-di-tert-butyl-N4, N9-bis(diphenylmethylene) pyrene-4,9-diamine (12.9 g, 0.0155 mol) in THF. The reaction mixture is agitated while refluxing for 6 hours. After the reaction is complete, it is cooled to room temperature (24° C.) and evaporated under a reduced pressure. The crude solid is washed with dichloromethane (DCM) and suspended in about 10 ml of MeOH and 50 ml of diethyl ether. The solid is filtered and washed with diethyl ether to give a product as a green solid (9.6 g, yield: 93%).

Example 3-2

Synthesis of N,N'-(5,10-dibromo-2,7-di-tert-butylpyren-4,9-diyl)dithiophene-2-carboxamide Diisopropylethyl amine (DIPEA) (10 mL) is added to a stirred solution of 5,10-dibromo-2,7-di-tert-butylpyrene-4,9-diamine (8.1 g, 0.012 mol) in dioxane. The reaction mixture is cooled to 0° C. and thiophene carbonyl chloride (3.89 mL, 0.036 mol, 3 eq) is added thereto. Then, the resultant is stirred at 70 ☐ for 3 hours. After the reaction is complete, it is cooled to room temperature (24° C.) and then, filtered and washed with diethyl ether and water several times, respectively. The solid is dried to give a product as a white solid (6.3 g, 72%).

Example 3-3

Synthesis of N,N'-(5,10-dibromo-2,7-di-tert-butylpyrene-4,9-diyl)dithiophene-2-carbothioamide Lawesson's reagent (19.6 g, 0.0485 mol, 5 eq) is added to a stirred solution of N,N'-(5,10-dibromo-2,7-di-tert-butylpyren-4,9-diyl)dithiophene-2-carboxamide (7 g, 0.0097 mol) in THF and toluene. The reaction mixture is agitated while refluxing overnight. After the reaction is complete, it is cooled to room temperature (24° C.) and evaporated under a reduced pressure. The crude solid is suspended in diethyl ether and stirred for 30 minutes. The resultant is filtered and dried to give a product as a yellow solid (7.3 g, quantitative).

Example 3-4

Synthesis of 2,6-di-tert-butyl-4,8-di(2-thienyl)-pyreno[4,5-b:9,10-b']dithiazole $Cs_2CO_3$ (9.3 g, 0.0286 mol, 3 eq) is added to a stirred solution of N,N'-(5,10-dibromo-2,7-di-tert-butylpyren-4,9-diyl)dithiophene-2-carbothioamide (7.2 g, 0.0095 mol) in DMF (120 mL). The reaction mixture is heated at 120 ☐ for 3 hours. After the reaction is complete, it is cooled to room temperature (24° C.) and water is added thereto. The precipitate is filtered and washed with dichloromethane (DCM) to give the product as a yellow solid (4.5 g, yield: 80%).
$^1H$ NMR (300 MHz, $CDCl_3$-TFA-d): δ (ppm) 9.20 (d, 2H), 8.54 (d, 2H), 8.27 (d, 2H), 8.06 (d, 2H), 7.44 (t, 2H), 1.61 (t, 18H).

Examples 4 and 5

Manufacture of Organic Thin Film Transistors

Firstly, a gate electrode of molybdenum is deposited at 1000 Å on a cleaned glass substrate by sputtering, and an insulation layer of $SiO_2$ is deposited thereon at 1000 Å by a CVD method. Then Au is deposited at 1200 Å thereon by sputtering to provide a source electrode and a drain electrode. The resultant substrate is washed for 10 minutes using isopropyl alcohol, and dried. Then the resultant substrate is immersed in an octadecyltrichlorosilane solution that is diluted in chloroform at a concentration of 10 mM, for 30 minutes, and it is washed with acetone and dried. The organic semiconductor polymers obtained from Example 1 and 2 are respectively dissolved in chlorobenzene to a concentration of 1.0 wt % to provide compositions for forming an active layer, and the compositions for forming an active layer are coated between the source electrode and drain electrode, using spin-coating, respectively and then baked at 150° C. for one hour under the nitrogen atmosphere to fabricate OTFT devices depicted in FIG. 1.

Example 6

Manufacture of Organic Thin Film Transistors

Firstly, a gate electrode of molybdenum is deposited at 1000 Å on a cleaned glass substrate by sputtering, and an insulation layer of $SiO_2$ is deposited thereon at 1000 Å by a CVD method. Then Au is deposited at 1200 Å thereon by sputtering to provide a source electrode and a drain electrode. The resultant substrate is washed for 10 minutes using isopropyl alcohol, and dried. The organic semiconductor compound according to Example 3 is vacuum-deposited between the source electrode and drain electrode to fabricate an OTFT device depicted in FIG. 1.

The OTFT devices according to Examples 4 to 6 are measured for current-transfer characteristics using a semiconductor characterization system (4200-SCS, KEITHLEY CORP.). Current-transfer characteristics are summarized in Table 1.

TABLE 1

|  | Charge mobility ($cm^2/Vs$) | Current on/off ratio ($I_{on}/I_{off}$) |
| --- | --- | --- |
| Example 1 | 0.001 | 7,000 |
| Example 2 | 0.002 | 20,000 |
| Example 3 | 0.22 | 300,000 |

The charge mobility of Table 1 is obtained from a slope of a graph of $(ISD)^{1/2}$ and $V_G$ parameters obtained from the following current Equation 1 in a saturation region.

$$I_{SD} = \frac{WC_0}{2L}\mu(V_G - V_T)^2 \quad \text{[Equation 1]}$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In the current Equation 1, $I_{SD}$ refers to a source-drain current, μ or $\mu_{FET}$ refers to charge mobility, $C_O$ refers to oxide layer capacitance, W is a channel width, L is a channel length, $V_G$ is a gate voltage and $V_T$ is a threshold voltage.

Current on/off ratio ($I_{on}/I_{off}$) is a ratio of an on-state maximum current value ($I_{on}$) with respect to an off-state minimum current value ($I_{off}$).

As shown in Table 1, the devices according to Examples 4 to 6 show improved charge mobility and current on/off ratios.

While this disclosure has been described in connection with some example embodiments, it is to be understood that other example embodiments are not limited to the disclosed embodiments, but, on the contrary, various modifications and equivalent arrangements may be made therein without departing from the spirit and scope of the appended claims. Therefore, the aforementioned example embodiments should be understood to be illustrative but not limiting in any way.

What is claimed is:

1. An organic semiconductor compound having a structure represented by the following Chemical Formula 2:

[Chemical Formula 2]

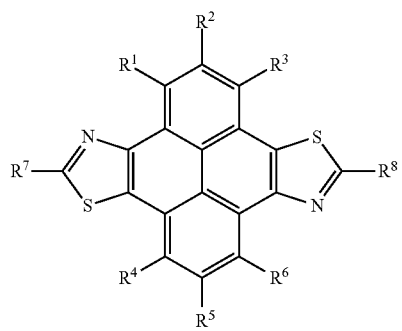

wherein, in the above Chemical Formula 2, $R^1$ to $R^6$ are each independently one of (i) hydrogen, a halogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C1 to C20 alkoxy group, a substituted or unsubstituted C3 to C20 cycloalkyloxy group, a substituted or unsubstituted C6 to C30 aryl group, a substituted or unsubstituted C6 to C30 aryloxy group, a substituted or unsubstituted heteroaryl group, a heteroaromatic ring wherein the heteroatom is at least one electron withdrawing imine nitrogen atom, a heteroaromatic ring wherein the heteroatom is at least one sulfur atom, $NR^{51}R^{52}$, $C(O)OR^{53}$, $C(O)NR^{54}R^{55}$, and (ii) structured so two adjacent substituents of $R^1$ to $R^6$ are linked to each other to provide one of a thiophenyl ring group fused with a pyrene moiety and a thiazolyl ring group fused with a pyrene moiety, wherein $R^{51}$ to $R^{55}$ are each independently one of hydrogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C6 to C30 aryl group, and a substituted or unsubstituted heteroaryl group, wherein the heteroaromatic ring wherein the heteroatom is at least one electron withdrawing imine nitrogen atom bonded to a functional group is one of the groups represented by the following Chemical Formula 3:

[Chemical Formula 3]

 (3-1)

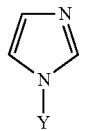 (3-2)

 (3-3)

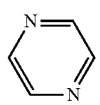 (3-4)

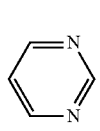 (3-5)

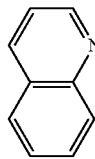 (3-6)

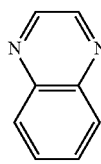 (3-7)

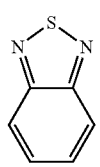 (3-8)

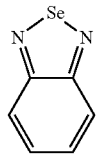 (3-9)

 (3-10)

 (3-11)

 (3-12)

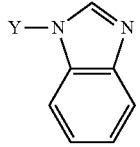 (3-13)

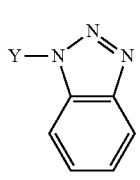 (3-14)

-continued (3-15)
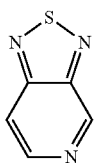

(3-16)
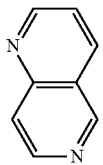

(3-17)
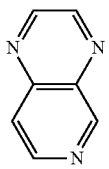

(3-18)
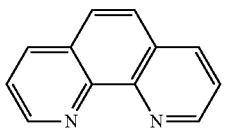

(3-19)
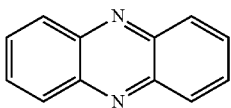

wherein, in the above Chemical Formula 3,

Y is one of hydrogen, a C1 to C20 linear or branched alkyl group, a C3 to C20 cycloalkyl group, a C6 to C30 aryl group, a C1 to C16 linear or branched alkoxy group, and a C3 to C16 cycloalkoxyalkyl group, wherein the heteroaromatic ring wherein the heteroatom is at least one sulfur atom is one of the groups represented by the following Chemical Formula 4:

[Chemical Formula 4]

(4-1)

(4-2)
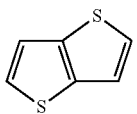

(4-3)
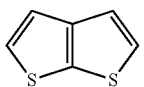

(4-4)
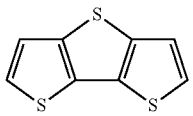

(4-5)
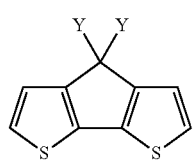

wherein, in the above Chemical Formula 4,

Y is one of hydrogen, a C1 to C20 linear or branched alkyl group, a C3 to C20 cycloalkyl group, a C6 to C30 aryl group, a C1 to C16 linear or branched alkoxy group, and a C3 to C16 cycloalkoxyalkyl group, and wherein, in the above Chemical Formula 2, $R^7$ and $R^8$ each independently are one of hydrogen, a halogen, a substituted or unsubstituted thiophene group, a substituted or unsubstituted bithiophene group, a substituted or unsubstituted benzothiophene group, a substituted or unsubstituted thienothiophene group, and a substituted heteroaromatic ring having at least one thiophenyl group.

2. The organic semiconductor compound of claim 1, wherein $R^7$ and $R^8$ comprise one of a thiophenyl group and a bithiophene group.

3. A transistor comprising the organic semiconductor compound according to claim 1.

4. The transistor of claim 3, further comprising:
a gate electrode on a substrate;
a source electrode and a drain electrode on the substrate, the source electrode and the drain electrode facing each other and defining a channel region;
an insulation layer on the substrate, the insulation layer electrically insulating the source electrode, the drain electrode, and the gate electrode; and
an active layer in between the source electrode and the drain electrode, the active layer including the organic semiconductor compound.

5. An electronic device comprising the organic semiconductor compound according to claim 1.

6. An organic semiconductor polymer having a structural unit represented by the following Chemical Formula 6:

[Chemical Formula 6]

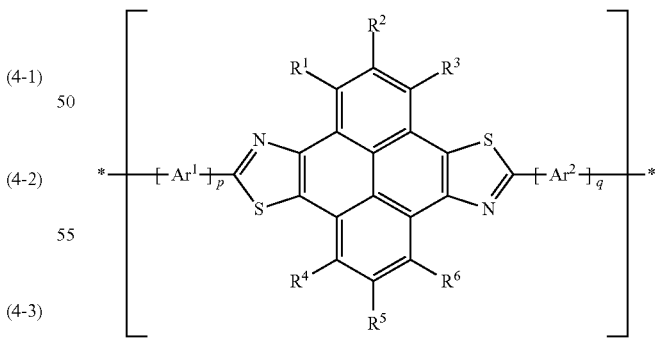

wherein, in the above Chemical Formula 6, $R^1$ to $R^6$ are each independently one of (i) hydrogen, a halogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C1 to C20 alkoxy group, a substituted or unsubstituted C3 to C20 cycloalkyloxy group, a substituted or unsubstituted C6 to C30 aryl group, a substituted or unsubstituted C6 to C30 aryloxy group, a substituted or unsubstituted heteroaryl group, a heteroaromatic ring wherein the heteroatom is at least one electron withdrawing imine nitrogen atom, a heteroaromatic ring wherein the heteroatom is at least one sulfur atom, $NR^{51}R^{52}$, $C(O)OR^{53}$, $C(O)NR^{54}R^{55}$, and (ii) structured so two adjacent substituents of $R^1$ to $R^6$ are linked to each other to provide one of a thiophenyl ring group fused with a pyrene moiety and a thiazolyl ring group fused with a pyrene moiety, wherein $R^{51}$ to $R^{55}$ are each independently one of hydrogen, a substituted C1 to C20 linear alkyl group, a substituted C1 to C20 branched alkyl group, an unsubstituted C1 to C20 linear alkyl group, an unsubstituted C1 to C20 branched alkyl group, a substituted or unsubstituted C3 to C20 cycloalkyl group, a substituted or unsubstituted C6 to C30 aryl group, a substituted or unsubstituted heteroaryl group, wherein the heteroaromatic ring wherein the heteroatom is at least one electron withdrawing imine nitrogen atom bonded to a functional group is one of the groups represented by the following Chemical Formula 3:

[Chemical Formula 3]

-continued

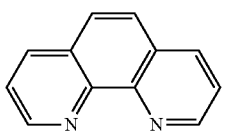
(3-18)

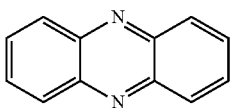
(3-19)

wherein, in the above Chemical Formula 3,
Y is one of hydrogen, a C1 to C20 linear or branched alkyl group, a C3 to C20 cycloalkyl group, a C6 to C30 aryl group, a C1 to C16 linear or branched alkoxy group, and a C3 to C16 cycloalkoxyalkyl group,
wherein the heteroaromatic ring wherein the heteroatom is at least one sulfur atom is one of the groups represented by the following Chemical Formula 4:

[Chemical Formula 4]

(4-1)

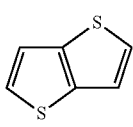
(4-2)

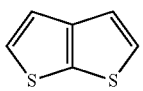
(4-3)

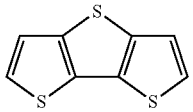
(4-4)

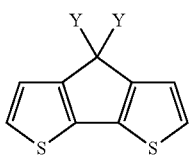
(4-5)

wherein, in the above Chemical Formula 4,
Y is one of hydrogen, a C1 to C20 linear or branched alkyl group, a C3 to C20 cycloalkyl group, a C6 to C30 aryl group, a C1 to C16 linear or branched alkoxy group, and a C3 to C16 cycloalkoxyalkyl group, and $Ar^1$ and $Ar^2$ each independently include one of a substituted or unsubstituted thiophene group, a substituted or unsubstituted bithiophene group, a substituted or unsubstituted thienothiophene group, and a substituted heteroaromatic ring having at least one thiophenyl group, p and q are each independently integers ranging from 0 to 10, and when p or q are each 2 or more, a plurality of $Ar^1$ and $Ar^2$ are the same or different from each other.

7. The organic semiconductor polymer of claim 6, wherein at least one of the $Ar^1$ and $Ar^2$ comprises a substituted heteroaromatic ring having at least one thiophenyl group and is represented by the following Chemical Formula 7:

[Chemical Formula 7]

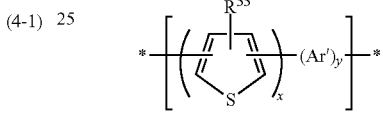

wherein, in the above Chemical Formula 7,
$R^{55}$ is one of hydrogen and a C1 to C20 alkyl group, $Ar^1$ is one of a C6 to C30 arylene group, a C6 to C30 condensed polycyclic group, heteroaromatic ring, and a heteroaromatic ring wherein the heteroatom is at least one electron withdrawing imine nitrogen atom, a heteroaromatic ring wherein the heteroatom is at least one sulfur atom, and x is an integer ranging from 1 to 7, and y is an integer ranging from 0 to 4.

8. The organic semiconductor polymer of claim 6, wherein the $Ar^1$ and $Ar^2$ comprises one of a substituted or unsubstituted phenylene group, a substituted or unsubstituted thiophene group, a substituted or unsubstituted benzothiophene group, and a substituted or unsubstituted thienothiophene group.

9. The organic semiconductor polymer of claim 6, wherein the organic semiconductor polymer includes one of the molecules represented by the following Chemical Formulae 8-3 to 8-4:

[Chemical Formula 8-3]

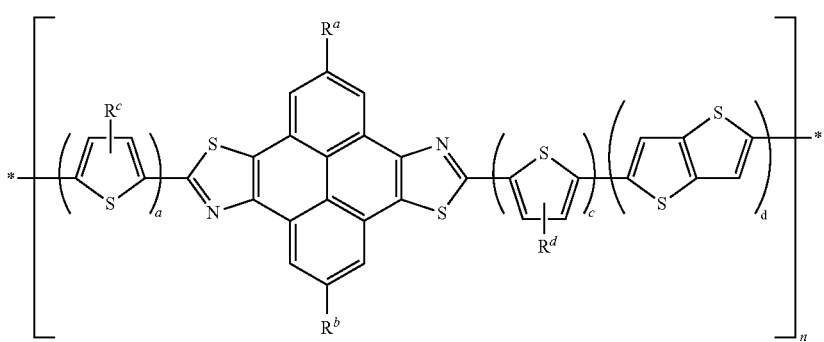

[Chemical Formula 8-4]

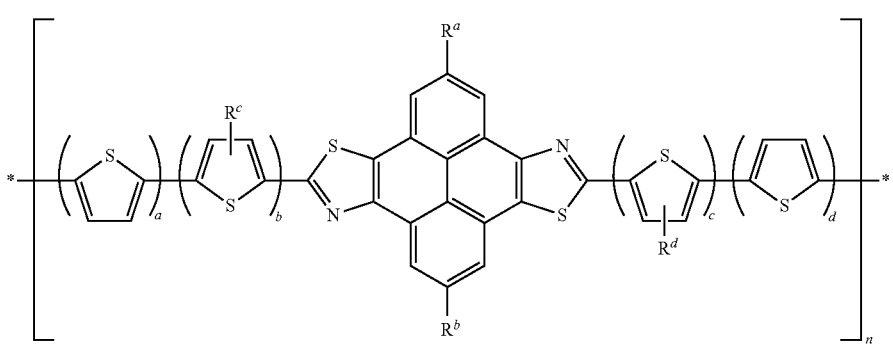

wherein, in Chemical Formulae 8-3 and 8-4, $R^a$ and $R^b$ are one of (i) a C1 to C10 alkyl group, and a heteroaromatic ring wherein the heteroatom is at least one electron withdrawing imine nitrogen atom, and (ii) $R^a$ or $R^b$ forms one of a thiophenyl ring group fused with a pyrene moiety and a thiazolyl ring group fused with a pyrene moiety, $R^c$ and $R^d$ are a C1 to C20 alkyl group, a, b, c, and d are integers ranging from 0 to 10, and a+b and c+d are 10 or less, and n is a polymerization degree of a polymer.

10. The organic semiconductor polymer of claim 6, wherein the organic semiconductor polymer has a number average molecular weight (Mn) of about 5000 to about 200,000.

11. The organic semiconductor polymer of claim 6, wherein the organic semiconductor polymer is a p-type organic semiconductor polymer.

12. A transistor comprising the organic semiconductor polymer according to claim 6.

13. The transistor of claim 12, further comprising:
a gate electrode on a substrate;
a source electrode and a drain electrode on a substrate, the source electrode and the drain electrode facing each other and defining a channel region;
an insulation layer on the substrate, the insulation layer electrically insulates the source electrode, the drain electrode, and the gate electrode; and
an active layer in between the source electrode and the drain electrode, the active layer including the organic semiconductor polymer.

14. An electronic device comprising the organic semiconductor polymer according to claim 6.

15. The organic semiconductor compound of claim 1, wherein $R^7$ and $R^8$ are each a thiophene group.

16. The organic semiconductor of claim 1, wherein $R^7$ and $R^8$ are each represented by the following Chemical Formula 14:

[Chemical Formula 14]

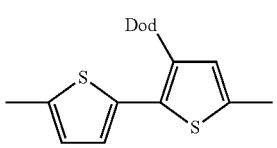

wherein, in the above Chemical Formula 14, Dod is a dodecyl group.

17. The organic semiconductor compound of claim 1, wherein $R^1$ to $R^6$ are hydrogen, $R^7$ and $R^8$ are each a thiophene group or a bithiophene group represented by the following Chemical Formula 14:

[Chemical Formula 14]

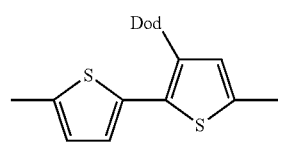

wherein, in the above Chemical Formula 14, Dod is a dodecyl group.

18. The organic semiconductor polymer of claim 9, wherein the one of the molecules represented the following Chemical Formulae 8-3 to 8-4 is represented by Chemical Formula 8-3, a and c are 1, and d is 0.

19. The organic semiconductor polymer of claim 9, wherein the one of the molecules represented the following Chemical Formulae 8-3 to 8-4 is represented by Chemical Formula 8-4, a, b, c, and d are 1, Rc and Rd are a dodecyl group.

20. The organic semiconductor polymer of claim 9, wherein a and c are 1, b and d are 0 or b and d are each 1, and $R^a$ and $R^b$ are hydrogen.

* * * * *